US010123869B2

(12) United States Patent
Blanckaert et al.

(10) Patent No.: US 10,123,869 B2
(45) Date of Patent: Nov. 13, 2018

(54) BIONIC EYE LENS

(71) Applicants: Johan Blanckaert, Ypres (BE); Christ Glorieux, Heverlee (BE); Robert Puers, Blanden (BE)

(72) Inventors: Johan Blanckaert, Ypres (BE); Christ Glorieux, Heverlee (BE); Robert Puers, Blanden (BE)

(73) Assignee: KATHOLIEKE UNIVERSITEIT LEUVEN, Leuven (BE)

( * ) Notice: Subject to any disclaimer, the term of this patent is extended or adjusted under 35 U.S.C. 154(b) by 1266 days.

(21) Appl. No.: 13/737,559

(22) Filed: Jan. 9, 2013

(65) Prior Publication Data

US 2013/0218270 A1 Aug. 22, 2013

Related U.S. Application Data

(63) Continuation-in-part of application No. PCT/BE2011/000045, filed on Jul. 12, 2011.

(30) Foreign Application Priority Data

Jul. 12, 2010 (GB) .................................... 1011627.5
Mar. 21, 2011 (GB) .................................... 1104689.3
Mar. 21, 2011 (GB) .................................... 1104692.7

(51) Int. Cl.
*A61F 2/16* (2006.01)
*A61B 5/11* (2006.01)
*A61B 5/00* (2006.01)

(52) U.S. Cl.
CPC .......... *A61F 2/1627* (2013.01); *A61B 5/1107* (2013.01); *A61B 5/6821* (2013.01);
(Continued)

(58) Field of Classification Search
CPC ................. A61F 2/1627; A61B 5/1107; A61B 2562/0223; A61B 5/6821
See application file for complete search history.

(56) References Cited

U.S. PATENT DOCUMENTS

| 4,373,218 A | 2/1983 | Schachar |
| 2007/0260307 A1 | 11/2007 | Azar |

(Continued)

FOREIGN PATENT DOCUMENTS

WO 10/004094 A1 1/2010

OTHER PUBLICATIONS

International Search Report and Written Opinion dated Nov. 23, 2011, in connection with International Application No. PCT/BE2011/000045, filed Jul. 12, 2011.

*Primary Examiner* — Howie Matthews
(74) *Attorney, Agent, or Firm* — Duane Morris LLP; J. Rodman Steele, Jr.; Gregory M. Lefkowitz

(57) ABSTRACT

The present invention relates generally to the restoration or improvement of the quality of human vision and, more particularly to a self-adapting system and method for achieving automatic sharp vision by the human eye of objects for instance at distances between 25 cm and more than 10 meters away. The invention can be situated in at least four technological domains: 1. ophthalmology, in particular the implantation of intraocular lenses. 2. Non-contact biometric signal recording and processing. 3. Electro-optic control of refractive lens power. 4. Wireless energy transfer.

20 Claims, 10 Drawing Sheets

(52) U.S. Cl.
CPC ......... *A61B 2562/0223* (2013.01); *A61F 2002/1699* (2015.04); *A61F 2250/0002* (2013.01); *A61F 2250/0096* (2013.01)

(56) References Cited

U.S. PATENT DOCUMENTS

2009/0204207 A1* 8/2009 Blum .................. G02C 7/08
 623/4.1
2010/0004741 A1 1/2010 Gupta

* cited by examiner

Cross section of circular lens geometry

BIONIC EYE LENS

CROSS REFERENCE TO PRIOR APPLICATIONS

This is a continuation-in-part of International Application PCT/BE2011/000045, with an international filing date of Jul. 12, 2011, which claims priority to Great Britain Patent Application No. 1011627,5, filed Jul. 12, 2010, Great Britain Patent Application No. 1104692.7, filed Mar. 21, 2011, and Great Britain Patent Application No. 1104689.3, filed Mar. 21, 2011, the entire contents of which are incorporated herein by reference.

FIELD OF THE INVENTION

The present invention relates generally to the restoration or improvement of the quality of human vision and, more particularly to a self-adapting system and method for achieving automatic sharp vision by the human eye of objects for instance at distances between 25 cm and more than 10 meters away.

BACKGROUND OF THE INVENTION

Several documents are cited throughout the text of this specification. Each of the documents herein (including any manufacturer's specifications, instructions etc.) are hereby incorporated by reference; however, there is no admission that any document cited is indeed prior art of the present invention.

The human eye consists of a composite lens system [T. Hellmuth Sensors Update 3(1), 289-223(2001)]. When light enters the eye, the cornea is the first lens encountered and has a large refractive power (typically 54-59 dioptry, refractive index 1.38). Behind the diaphragm or iris the light is refracted by a second lens (refractive index 1.41) with variable dioptry in view of accommodating [T. Missotten et al., Journal of Cataract and Refractive Surgery 30(10), 2084-2087 (2004)], i.e. finely adjusting the dioptric strength of the lens (typically between 0 and 4 dioptry) in order to focus the view on an object at given distance and thus getting a sharp image on the retina, which collects the light that leaves the second lens and reaches the retina via the vitreous humor (refractive index 1.34). In natural circumstances the strength of the second lens is adjusted by shape changes induced by (de-) contractions of the ciliary muscle around the ciliary muscle. The state of the ciliary muscle is controlled by the brain via the muscle nerves. The motoric part of the brain is hereby continuously receiving signals via the optic nerve front the visual cortex in order to steer the ciliary muscle so that sharp vision is obtained for the object under inspection. Since the system acts as a closed, iterative feedback loop, the system ensures sharp vision at every time provided that the required refractive lens power lies within the dynamic range of the ciliary muscle-lens system, and provided sufficient time is provided to process the visual information and adjust the ciliary muscle.

As the age of a person increases, typically starting from 45 years and above, the fibers of the accommodating lens lose their elasticity so that the dioptric range is reduced, inhibiting the eye to focus on objects at short distances, in spite of a perfectly functioning (typically during the whole lifetime of a person) ciliary muscle. Typically people solve this problem by using glasses or contact lenses with positive dioptry when necessary.

In the case of cataract disease, the variable lens becomes milky, leading to a reduction transparency and blurred vision. A partial cure of this problem is achieved by replacing the natural lens by an artificial one, whose dioptry is chosen (lenses with strengths between −10 and +35 dioptry are commercially available) that the eye lens assembly in rest gives a sharp focus at very long distances. A standard artificial lens is monofocal and accommodation is no longer possible. Glasses are necessary to provide sharp vision at intermediate distances, in particular at reading distance. Multifocal artificial lenses also exist, providing simultaneous sharp vision at multiple distances. The brain is then subconsciously 'choosing' which image information out of the composite multifocal image it is processing. However, since at any time a multifocal lens is projecting images from different focal distances on the retina, every sharp object (in particular in a dark environment in the presence of strong light sources) is surrounded by a blurred halo or glare. In addition, the distribution by a multifocal on multiple focal points leads to a contrast reduction.

Ideal restoration of the accommodative power of a human eye suggests the design of a self-adjusting variable lens. This concept has been shown by automatically accommodating spectacles [G. Li, D. L. Mathine, et al. Proceedings of the National Academy of Sciences of the United States of America, PNAS published online Apr. 5, 2006; doi; 10.1073/pnas.0600850103], in which the dioptric power of the glasses was electro-optically adjusted (cfr autofocus of a digital camera), depending on the conscious choice of the user. This solution is obviously not equivalent to the truly ideal natural way of vision, i.e. the automatic self-accommodating intraocular lens, which sub-consciously self-adjusts to get a sharp image of the object under inspection. Also, the refractive power of liquid crystal based electro-optic spectacle lenses is polarization dependent, leading to partial image blur and halo and glare effects.

Also progress has been made on intraocular solutions for a self-adapting lens that makes use to a maximum extent of the naturally available anatomical tools. A possible system contains an intraocular lens that is mounted such that its shape (or position) and thus refractive power (in combination with a second intra-ocular lens), is mechanically determined by the state of the ciliary muscle. In this way the functionality of the natural eye lens is restored. However, it turns out that this system is problematic, because typically for most patients the elasticity of the lens diaphragm is distorted, thus deteriorating the mechanical control of the adaptive lens by the ciliary muscle.

Related to the control of the refractive power of the eye, some techniques exist to detect the state of the eye. Opthalmological apparatus exist to determine the width of the iris, to visualize the ciliary muscle, and to determine the refractive power of the eye lens assembly. These techniques are based on the optical access via the iris, and on ultrasonic echography. A solution is by determining the eye ball pressure via inserted electrodes. However, no techniques have been proposed to electronically monitor the state of the ciliary muscle. Neither have there been proposals for building and energetically maintaining stand-alone electronic circuitry in the eye ball.

There is thus a need in the art for an intra-ocular lens whose refractive power is controlled in a seamless manner by a signal that is representative for the state of the ciliary muscle, or other muscular signals, or other positional markers that reflect to which direction the visual cortex wants to change the eye lens dioptry, and for the detection of that signal. There is also a need for a wireless method to continuously or frequently supply energy to the intraocular device from a device located out of the human body, and for a small intraocular device that receives, stores and releases this energy.

The present invention comprises an intraocular lens with electro-optically controlled refractive power that can be surgically placed. By making use of a dual lens assembly and a hybrid lens design that makes use of electronically controlled liquid crystal alignment on one hand and a curved (e.g. concave) lens shape on the other hand, the refractive power of intra-optic lens is made polarization independent, resulting in optimum focus for near to 100%, for instance more than 98%, preferably more than 99%, of the incident light, with minimum light loss due to reflection and absorption. This solves the glare and halo problems in the current state of the art. The curved lens shape allows the use of easy to produce uniform electrodes. Without voltage applied over the electrodes of the first lens ("lens L1"), the liquid crystal is aligned in a planar way due to the presence of a thin, transparent aligning layer on top of the transparent electrode. When the voltage over the electrodes is increased, the liquid crystal alignment tends more and more to homeotropic alignment. As a result, the effective refractive index of the liquid crystal layer for one of the two polarization components ("component P1") of the incident light is monotonously changed with the applied voltage. In combination with the curvature of one of the interlaces between the liquid crystal with the surrounding material, the change of refractive index results in a change of dioptric strength of the assembly for this polarization component. The dioptric strength of the other (orthogonal) polarization component ("component P2") is not affected by the voltage changes over lens L1. The second liquid crystal lens ("lens L2") assembly is placed in series with the first one. The planar alignment direction of the second lens is chosen perpendicular to the planar alignment of the first lens. As a consequence, lens L2 affects the dioptric strength for P2 and not for P1. Thus, together, L1 controls the dioptric strength of P1 and L2 controls the dioptric strength of P2. In this way, the dioptric strength of 100% of the light is controlled.

The steering signal for the refractive power control used in this invention is based on the electromagnetically detected position of a marker, which is placed in such a position so that this position is representative for the direction in which the visual cortex wants to change the dioptric strength in order to get a sharp image. In other words, in an embodiment of present invention an electromagnetically detected position of a marker, which is representative for an optic nerve signal from the visual cortex generated from neuronal processed spatiotemporal features and to change the dioptric strength in order to get a sharp image, is translated in the system or device of present invention into a time-varying voltage or current that conveys information that is a steering signal to control the refractive power of the lens. The electronic detection system or parts or elements of the electronic detection zone are preferably located in the peripheral zone of the artificial intraoptic lens, out of the transparent zone which transmits the light from the outside world to the retina.

The principle of detection is based on the monotonic relation between one or more of the marker positional coordinates, and the electric impedance of an inductive element comprised in a detector system, consisting for instance of at least one inductive coil or a wired inductive material or deposited metal structure on a printed circuit board, or of a Hall sensor located in the detection system.

On one hand the electric impedance of the inductive element or elements, for instance the detection coil, is electronically monitored by placing the inductive element for instance the coil in an appropriate electronic circuit (e.g. an amplitude (AM) or frequency (FM) detection circuit whose details are described further on). On the other hand, the electromagnetic field, around of the inductive elements or elements, for instance around the coil, and thus the inductive elements' for instance coil's electric impedance, is influenced by the electromagnetic properties of its environment, and in particular on the electric and magnetic properties of the marker, and on the marker position. Thus, changes in the marker's position, are reflected in changes in the electronic detector signal, and the other way around. The electric and magnetic properties, as well as the placement of the marker, are optimized in order to maximize the sensitivity of the impedance based signal to the marker's positional changes.

A particular specific embodiment of present invention concerns sensing the electric impedance of a detection coil whereby the coil is electronically monitored by an electronic circuit (e.g. an amplitude (AM) or frequency (FM) detection circuit whose details are described further on). Hereby the. electromagnetic field around of the coil, and thus the coil's electric impedance, is influenced by the electromagnetic properties of its environment, and in particular by spatiotemporal features of a marker that has an electrical conductivity or magnetic susceptibility different from the surrounding medium.

The above can be integrated in various schemes or embodiments.

In a first scheme embodying the present invention, the marker is surgically placed so that it is comprised in or is on the ciliary muscle, or near to it, in the zonular fiber connection zone between the ciliary muscle and the lens body. The ciliary muscle or the ring of striated smooth muscle in the eye's middle layer (vascular layer) that controls lens accommodation and that enabling changes in lens shape for light focusing. A marker placed on such ciliary muscle will change in spatiotemporal features during visual cortex instructed lens accommodation. A marker position near to the ciliary muscle is in the meaning that it is in or on a surrounding tissue so that during visual cortex instructed lens accommodation the spatiotemporal features are modified so that they are representative for the state of the ciliary muscle, or other muscular signals, or other positional markers that reflect to which direction the visual cortex wants to change the eye lens dioptry, and for the detection of that signal. In this way, (de)contractions of the ciliary muscle (which are representative for the focal changes desired by the visual cortex) result in changes of the relative position of the marker with respect to the detection coil. Hence, the electronic detection coil signal can be used as a measure of the ciliary muscle contraction and of thus of the intention of the visual cortex, in order to adjust, via an electronic interface between the detection system and the electro-optic system, the refractive power of the intraoptic lens. This mechanism restores the natural feedback system of focusing on objects whose position is varying over a wide range of distances, where the visual cortex plays the role of monitoring the sharpness of the image, and adjusting accordingly the refractive power of the eye lens.

In a second scheme or embodiment of the invention, the electronic detection system, in total of in part or its core, is still located in the peripheral zone of the artificial intraoptic lens, preferably out of the transparent zone which transmits the light from the outside world to the retina. However, the marker is surgically (subcutaneously) or externally placed (attached to the skin) in the region between both eyes, or even elsewhere on the head, not too far away from the eye ball in which the detection circuitry is residing, e.g. subcutaneously or attached to the skin on the temple of the person's head, or inside of spectacles. Unlike in the first scheme, in this case the relative position of the marker with respect to the inductive element, for instance the detection coil, is quasi independent of the state of the ciliary muscle. For this second system of detection, we make use of the following, alternative mechanism. When a person wants to focus on a nearby object, then, besides a ciliary muscle contraction, there is also a visual cortex controlled turning-in of the eye balls towards the central axis in the vision direction. The degree of turning-in is proportional with the intended degree of focusing. The turning-in also goes along with a change of relative position between the intraocular detection system, which is inside of the turning-in eye ball and thus following the eye movement, and the marker, which has a fixed position with respect to the person's head. Therefore, the impedance of the inductive element, for instance the detection coil which is electronically determined by the detection circuit, and which is sensing the distance between marker (fixed position) and eye ball (position dependent on the distance of the object of interest), is a measure for the intention of the visual cortex in terms of refractive power. Thus, as in the first scheme, this signal can be used to close the adaptive feedback loop that controls the dioptric strength of the eye lens in order to keep focused on objects of interest.

In a third scheme which is an embodiment of the invention, one or more markers and/or detection systems are placed in both eyes. The turning-in of the eyes then also is reflected in the relative positions between markers and detection systems, so that the derived impedance signals can be used for dioptric control in the electro-optic circuitry. In the following, the electronic scheme to measure the impedance (or changes of the impedance) of the inductive element is described in more detail e.g. the detection coil, and its geometry and placement. In this invention, the impedance (changes) is detected by putting the inductive element, for instance the coil (inductance) in an electric oscillator circuit (e.g. a Colpitts oscillator). The resonance frequency of this circuit then monotonically depends on the inductance (and thus impedance) of the inductive element, e.g. the coil. This resonance frequency can then be derived using an FM detection system, e.g. a phase locked loop circuit (PLL) or frequency to voltage converter (PVC). Alternatively, the frequency of the oscillator circuit can be forced, such that changes of the impedance are transformed into amplitude changes of the oscillator voltage, so that classical electronic circuits for AM demodulation can be used, e.g. lock-in amplifier type of circuits.

Given the need for optical transmission in the middle part of the lens implant, only the peripheral zone of the lens body can be used to put electronic circuitry. This is depicted in the figures. Different schemes are possible for the geometry and positioning of the coil, e.g. the coil can be planar or cylindrical, it can be parallel with or perpendicular to the equator plane, and a dual coil with or without differential detection can be used in order to enhance the sensitivity and directivity of the detection or changes in the environment, and the selectivity to detect the marker (and not possible other motions of electromagnetically active objects in the neighborhood).

The material for the marker should be such that it has a maximum impact on the electromagnetic field, and thus electric impedance of the inductive element, for instance the coil, e.g. the markers are ferromagnetic and/or paramagnetic and or electrically conducting.

In an alternative scheme of this invention, instead of inductive detection, the position of a para- or ferromagnetic marker can be detected by a Hall probe that monitors the strength of the magnetic field of the marker, and thus its positional changes. This can be replaced in above-mentioned embodiments wherein in such case the markers are para- and/or ferromagnetic marker and their position or spatiotemporal features are detected by such Hall probe.

In yet another alternative embodiment of present invention, the marker is an inductive element (e.g. coil), and the detection is based on the principle of mutual induction between this element and the intraoptic detection circuit. Also here, positional changes of the marker coil are reflected in electronic signal changes in the detection circuit. The previous embodiments mentioned in this application can be adapted by this scheme. This invention also generally solves related issues of biometric sensing of the state of muscles.

In an alternative embodiment of present invention at least one Hall sensor detects the position of the ciliary muscle marker tag.

In another alternative, the incentive of the visual cortex to adjust the dioptric strength of the eye lens is determined by inductively sensing (or sensing via a Hall sensor) within the intraocular lens circuitry the relative distance of the eyeball to a metal piece between the eyes, and thus the angular orientation of the eye ball, which is a known measure for the distance to which a person wants to focus his or her view.

In a particular embodiment the intra-ocular and biocompatible miniaturized electro-optic device is supplied of energy from a device out of the body, in particular by a (near infrared, invisible) light transmitter in front of the eye to a solar cell on the eye lens, and by inductive electromagnetic transmission of AC electromagnetic energy from a coil in front of or around the eye or person's head (e.g. in the person's sleeping pillow) to a coil on the intraocular lens.

In a particular embodiment the intra-ocular and biocompatible miniaturized electro-optic device is supplied of energy from a device out of the body, in particular by a light transmitter, for instance by a near infrared, invisible, light transmitter in front of the eye to a solar cell on the eye lens, and by inductive electromagnetic transmission of AC electromagnetic energy from a coil in front of or around the eye to a coil on the intraocular lens.

In a particular embodiment the lens is a lens assembly of two plane parallel lenses (having opposite surfaces exactly plane and parallel) with a radial refractive index gradient, depending on optical thickness of the liquid crystal (LC) layer between two opposite lenses the focal distance of this assembly will vary.

In yet another particular embodiment the lens is a curved lens with a patterned hole electrode for an electrical field gradient, and thus a gradient in refractive index, which in turn results in voltage controllable refractive power.

SUMMARY OF THE INVENTION

Present invention provides a self-adaptive artificial lens with intact availability during all their life of people's brain which interprets and processes the sharpness of an image by the brain, to send an appropriate signal to the ciliary muscle, and for the ciliary muscle to (de-)contract accordingly. Our invention concerns an artificial insert of a novel signal conversion mechanism (B) of the ciliary muscle contraction into an appropriate change of dioptric strength of a novel artificial lens (A). Together with the image processing and ciliary muscle steering by the visual cortex, the ciliary muscle contraction motion detector and the intra-optic lens act as a closed feedback loop allowing the person to focus on images at distances between 25 cm and infinity. Some embodiments of the invention are set forth in claim format directly below: The system or device of present invention involves in diverse embodiments non-contact biometric signal recording and processing, electro-optic control of refractive lens power and wireless energy transfer. The system or device is suitable for ophthalmologic applications, in particular for the implantation of intraocular lenses and the creation of bionic eyes.

Present invention concerns an embodiment on an eye implantable unit of an intraocular device or intraocular implant system with an electro-optic self-adaptive artificial lens which comprises 1) signal conversion mechanism that converts ciliary muscle contraction into an appropriate change of dioptric strength of 2) an electro-optic artificial lens assembly comprising a transparent liquid-crystal display, consisting of a liquid crystal confined between transparent uniform electrode coated lenses, with a refractive index that is changed if an AC voltage, electronically controlled on the basis of the contraction state of the ciliary muscle, is applied between the electrodes so that the dioptric strength of the assembly is changed in a similar way as a natural, mechanically modified eye lens would due for the same ciliary muscle contraction, thus making possible a feedback system where on the basis of the sharpness of the image processed in the visual cortex, via the ciliary muscle signal, the dioptric strength of the electro-optic eye lens assembly is continuously adapted.

A first aspect of the present invention is the realization of an eye implantable unit of an intraocular device or intraocular implant system with an electro-optic self-adaptive artificial lens which comprises 1) signal conversion mechanism that converts inductively detected ciliary muscle contraction into an appropriate change of dioptric strength of 2) an electro-optic artificial lens assembly comprising a transparent liquid-crystal display, consisting of a liquid crystal confined between transparent uniform electrode coated lenses, with a refractive index that is changed if an AC voltage, electronically controlled on the basis of the contraction state of the ciliary muscle, is applied between the electrodes so that the dioptric strength of the assembly is changed in a similar way as a natural, mechanically modified eye lens would due for the same ciliary muscle contraction, thus making possible a feedback system where on the basis of the sharpness of the image, processed in the visual cortex, via the ciliary muscle signal, the dioptric strength of the electro-optic eye lens assembly is continuously adapted.

A second aspect of the present invention is the realization of an eye implantable unit of an intraocular device or of an intraocular implant system comprises 1) an electro-optic self-adaptive artificial lens assembly comprising at least one electrode and a refractive liquid-crystal display assembly with changeable refractive index and 2) a signal conversion mechanism adapted to convert ciliary muscle contraction into a proportional change of voltage signal adapted by the voltage change on the electrode to induce a change in dioptric power or change of dioptric strength of said artificial lens.

A third aspect of the present invention is the realization of an electro-optical implant assembly, the implant assembly comprising 1) an electronic detector system or device which has a motion detector element and a 2) an electro-optic artificial lens assembly and further comprising 3) a marker element having a marker or markers adapted to induce electric impedance variation on the motion detector element in relation to the positional modification or in relation to the spatiotemporal features of said marker element versus detector system to convert the electric impedance variation into a change of dioptric strength of the electro-optic artificial lens assembly.

A fourth aspect of the present invention is the realization of an eye implant system having an implantable unit according to the first or second aspect of the present invention configured to function with an external energy source.

A fifth aspect of the present invention is the realization of a totally implantable eye implant system having an implantable unit according to the third aspect of the present invention.

A sixth aspect of the present invention is the realization of an intraocular device according to a first or second aspect of the present invention, which is wireless connectable to an energy providing means (energizing device) to supply energy from a device out of the body, preferably comprising a (near infrared, invisible) light transmitter in front of the eye to a solar cell on the eye lens and by inductive electromagnetic transmission of AC whereby the energizing device is a coil in front of or around the eye to a coil on the intraocular lens to provide electromagnetic energy.

A seventh aspect of the present invention is the provision of a medical device of any one of the first, second, third, fourth, fifth and sixth aspects of the present invention for use in a treatment to restore or improve the quality of human vision.

An eighth aspect of the present invention is the provision of a medical device of any one of the first, second, third, fourth fifth and sixth aspects of the present invention for use in a treatment for achieving automatic sharp vision by the human eye of objects e.g. at distances between 25 cm and more than 10 meters away.

A ninth aspect of the present invention is the provision of the use of the system, device or system of any one of the first, second, third, fourth, fifth, sixth, seventh and eighth aspects of the present invention to process by the electronic detector system spatiotemporal changes in the ciliary muscle and proportional changes in the dioptric strength of the artificial lens so that an appropriate neuronal signal is sent to the ciliary muscle to (de-) contract accordingly after the sharpness of an image is interpreted and processed by the brain and so that so that the artificial lens focuses the image-sharply onto the retina.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description. It is to be understood that both the foregoing general description and the following detailed description are exemplary and explanatory only and are not restrictive of the invention, as claimed.

BRIEF DESCRIPTION OF THE DRAWINGS

The same reference numbers in different drawings identify the same or similar elements.

DETAILED DESCRIPTION

Figure 1A:
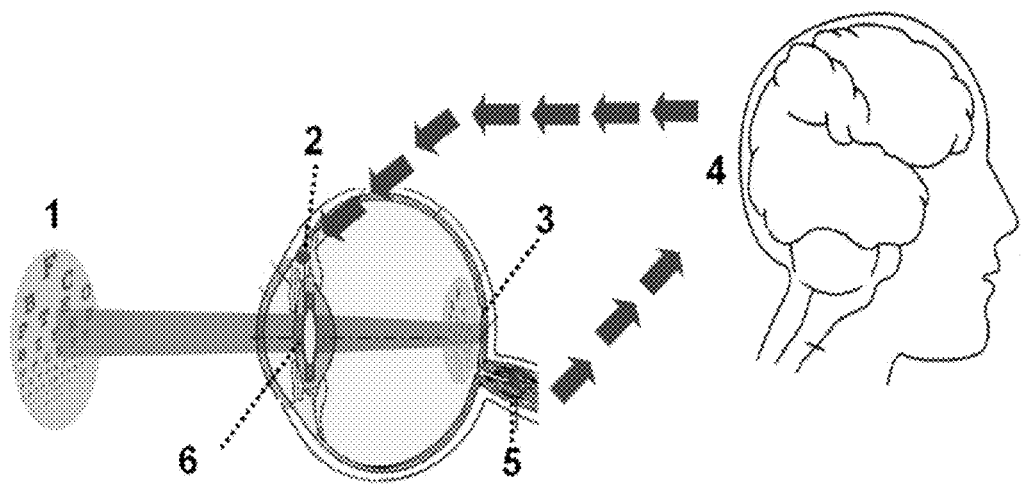
In FIG. 1(a) [1] is the object to focus on, [2] is the ciliary muscle with marker, [3] is the retina, [4] is the visual cortex, [5] is the optical nerve and [6] is the bionic eye lens and electronic detection and control circuitry.

Detailed Description of Embodiments of the Invention

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention.

Furthermore, the terms first, second, third and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence, or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B. The meaning of the word "comprising" encompasses all the specifically mentioned features as well as optional, additional, unspecified ones, whereas the term "consisting of" only includes those features as specified in the claim. Therefore, "comprising" includes the term "consisting of", so that the amendment from the former into the latter term does not extend beyond the content of the application as originally filed.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description, are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

Furthermore, some of the embodiments are described herein as a method or combination of elements of a method that can be implemented by a processor of a computer system or by other means of carrying out the function. Thus, a processor with the necessary instructions for carrying out such a method or element of a method forms a means for carrying out the method or element of a method. Furthermore, an element described herein of an apparatus embodiment is an example of a means for carrying out the function performed by the element for the purpose of carrying out the invention.

In the description provided herein, numerous specific details are set forth. However, it is understood that embodiments of the invention may be practiced without these specific details. In other instances, well-known methods, structures and techniques have not been shown in detail in order not to obscure an understanding of this description.

The following terms are provided solely to aid in the understanding of the invention.
Definitions The expression "electronically connected", as used in disclosing the present invention refers to the connection to an electromagnetic marker tag (e.g. ferromagnetic or metallic particles) dispersed in the ciliary muscle tissue and embraces both physical connection via circuitry and electromagnetic connection in a wireless manner via inductive (coil) or magnetic (Hall sensor) sensing e.g. signal transfer from the ciliary muscle to the lens controller by a non-contact mechanism, in which the changes of the state, i.e. the radial contraction distance, of the ciliary muscle, containing a ferromagnetic or metallic tracer particle attached to said ciliary muscle, are monitored by the induced electric inductance changes in a sensing coil placed on the intra-optic lens to translate a particular design, radial motions of the tracer particle are translated into proportional inductance changes. The expression "electronically connected" can also refer to the connection in which the changes of the state, i.e. the radial contraction distance, of the ciliary muscle, containing a ferromagnetic or metallic tracer particle attached to said ciliary muscle, can also be monitored by Hall voltage changes in a Hall sensor on the intra-optic lens. A further example, is the electronic and remote derivation of a steering signal proportional to the state of the ciliary muscle from the inductance of the coil generated by the changes in inductance of the sensing coil on the intra-optic lens due to positional changes of the magnetic, metallic or coil tag on the ciliary muscle, interaction and recovering the information content of the inductance by electronic demodulation circuitry to obtain a signal that is proportional to the position of the muscle marker tag. Another example of wireless electronic connection is the determination of the incentive of the visual cortex to adjust the dioptric strength of the eye lens by inductively sensing (or sensing via a Hall sensor) within the intraocular lens circuitry the relative distance of the eyeball to a metal piece between the eyes, and thus the angular orientation of the eye ball, which is a known measure for the distance to which a person wants to focus his or her view.

The following detailed description of the invention refers to the accompanying drawings. Also, the following detailed description docs not limit the invention. Instead, the scope of the invention is defined by the appended claims and equivalents thereof.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

The present invention will become more fully understood from the detailed description given herein below and the accompanying drawings which are given by way of illustration only, and thus are not limitative of the present invention.

Figure 1B:
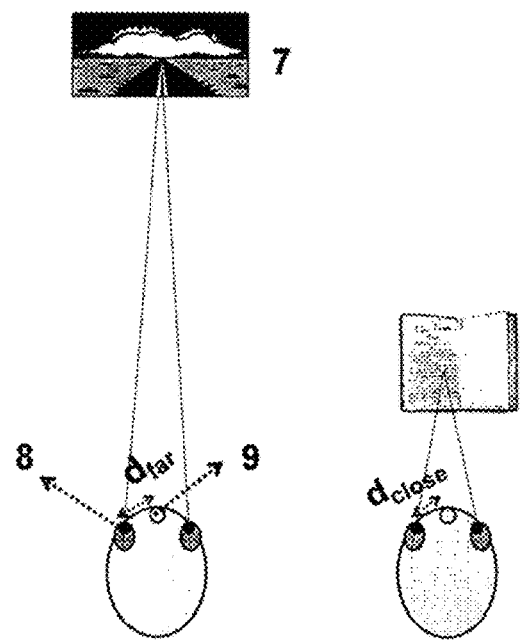
In FIG. 1(b) [7] is a far away object, [8] is an intraoptic lens with marker distance detection circuitry, [9] is a marker, [10] displays no "turning in" eye rotation and [11] displays "turning-in" eye rotation, in FIG. 1(c) [7] is a far way object, [12] is a close object, [13] is the eye ball, [D1] is the distance of the far object, [D2] is the distance of the close object and [D3] is the eye-marker distance.
Figure 1C:
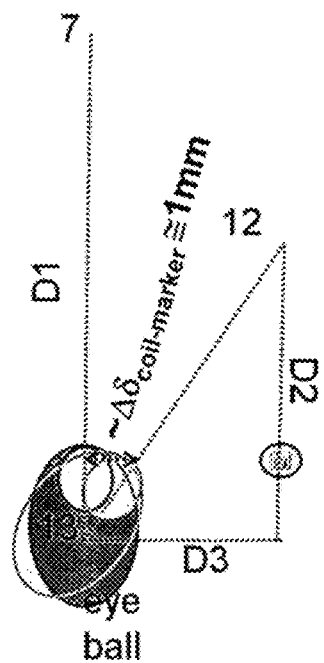
FIG. 1 is a graphic display providing the conceptual principle of the blonde eye lens.

FIG. 1 is a graphic display which provides the conceptual principle of the bionic eye lens. FIG. 1(a) [1] is the object to focus on, [2] is the ciliary muscle with marker, [3] is the retina, [4] is the visual cortex, [5] is the optical nerve and [6] is the bionic eye lens and electronic detection and control circuitry. In FIG.(b) [7] is a far away object, [8] is an intraoptic lens with marker distance detection circuitry, [9] is a marker, [10] displays no "turning-in" eye rotation and [11] displays "turning-in" eye rotation, F.(c) [7] is a far way object, [12] is a close object, [13] is the eye ball, [D1] distance of the far object, [D2]distance of the close object and [D3] eye-marker distance, which can be about 35 mm for instance between 30 and 40 mm. In order to see an object sharply by projecting the image of the object on the retina, the artificial lens should have an appropriate dioptric strength D. The object is continuously kept in focus by continuously adjusting the dioptric strength according to the inductive coil signal in the detection circuitry, which is a measure for the marker-coil distance d. The distance d in turn is proportional with dioptric strength targeted by the visual cortex. The latter is based on the following, (a) Marker in the ciliary muscle. If an object is out of focus, then the visual cortex sends a neuronal signal to the ciliary muscle to release or contract, and thus to make a natural eye lens more or less curved. In this case, the natural lens has been replaced by an artificial one. However, the state of the ciliary muscle is still representative for the incentive of the visual cortex. The electromagnetic detection circuitry around the artificial lens is remotely detecting changes in the state of contraction of the ciliary muscle via the changes in impedance of the defection coil, which are proportional with changes in distance (between the values $d_{close}$ and $d_{far}$ between the coil and the marker inside of the ciliary muscle. These changes are then accordingly translated by the electronic circuit into changes of the dioptric strength of the electro-optic lens, (b) Marker M on a fixed location between the eyes (or on a fixed location elsewhere, but close to the artificial eye lens circuitry. The more nearby is an object that a person is looking at, the more the eye balls are rotating inwards, keeping their axis directed towards the object. In this way the rotational position of the eye balls is a measure for the distance of the object to focus on, so that it can serve as a guide for the electro-optic control circuit to change the dioptric strength of the artificial lens. Changes in rotational position of the eye ball go along with a change in distance between the marker which is positioned on a fixed location in between the eyes, and the electromagnetic detection coil that is rotating together with the eye ball. In this way, changes in the inductive coil signal can be converted into changes in dioptric strength. In the case (c) where the bionic eye lens (with detection coil) is located 5 mm from the eye rotation centre, the variation in distance $\Delta\delta$ between the detection coil and the marker (e.g. placed subcutaneous above the nose, at 35 mm from the eye ball center) from the eye ball steering at an object very far away towards steering at an object at 25 cm distance is $tg\theta=35$ mm/250 mm=$\Delta\delta/5$ mm, so that $\Delta\delta=0.7$ mm.

Figure 2:
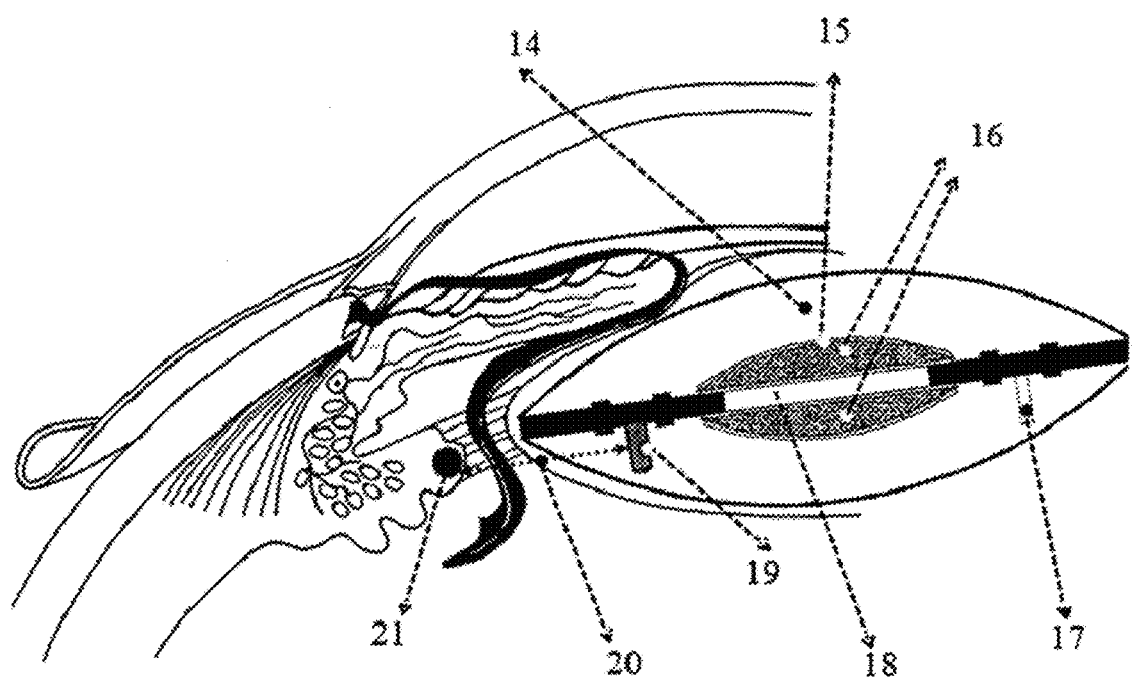
FIG. 2 shows a cross section of the eye ball with an artificial bionic eye lens assembly, where [14] is the lens body, [15] is the electrode and alignment layer. [16] are the liquid crystals with refractive index n so that $n_{//} \le n \le n_\perp$, and the liquid crystal is aligned according to polarization component $P_1$ (top) and $P_2$ (bottom, $\perp P_1$), [17] is an optional secondary detection coil, [18] is the transparent layer, [19] is the (primary) detection coil, [20] is the marker-coil distance and [21] is the marker in the ciliary muscle.

FIG. 2 displays a cross section, of the eye ball with an artificial bionic eye lens assembly. Hereby [14] is the lens body, [15] is the electrode and alignment layer. [16] are the liquid crystals with refractive index n so that $n//\leq n \leq n_\perp$, and liquid crystal aligned, according to polarization component $P_1$ (top) and $P_2$ (bottom, $\perp P_1$, [17] is an optional secondary detection coil, [18] is the transparent layer, [19] is the (primary) detection coil, is the marker-coil distance and [21] is the marker in ciliary muscle. The marker moves along with the ciliary muscle, which is controlled by the visual cortex. The state of contraction of the muscle, and thus the distance d between the marker attached to the muscle and the detection coil in the bionic eye lens assembly, is determined by monitoring the electric impedance of the detection coil, which changes proportional with d. The electronic circuitry is placed in the peripheral region in the equatorial plane of the lens. The electric impedance of the coil in the detection circuitry is proportional with the distance between the intraocular device and the marker, and thus a measure for the target, dioptric strength $D_{target}$ envisaged by the visual cortex. In the configuration shown, the marker is placed in the ciliary muscle, thus acting as part of a system sensing the state of contraction of the ciliary muscle, which is proportional with $D_{target}$. The figure shows an example of the placement of the detection coil inside of the bionic eye lens assembly. The coil is placed sideways out of the optical path. The axis can be oriented towards the marker, in order to optimize the detection sensitivity. Also two coils/oscillator circuits can be used, in order to increase the detection sensitivity in the (marker) region of interest, and to remove artifact background effects of metallic or magnetic objects in the neighborhood, by means of a differential detection scheme.

Figure 3:
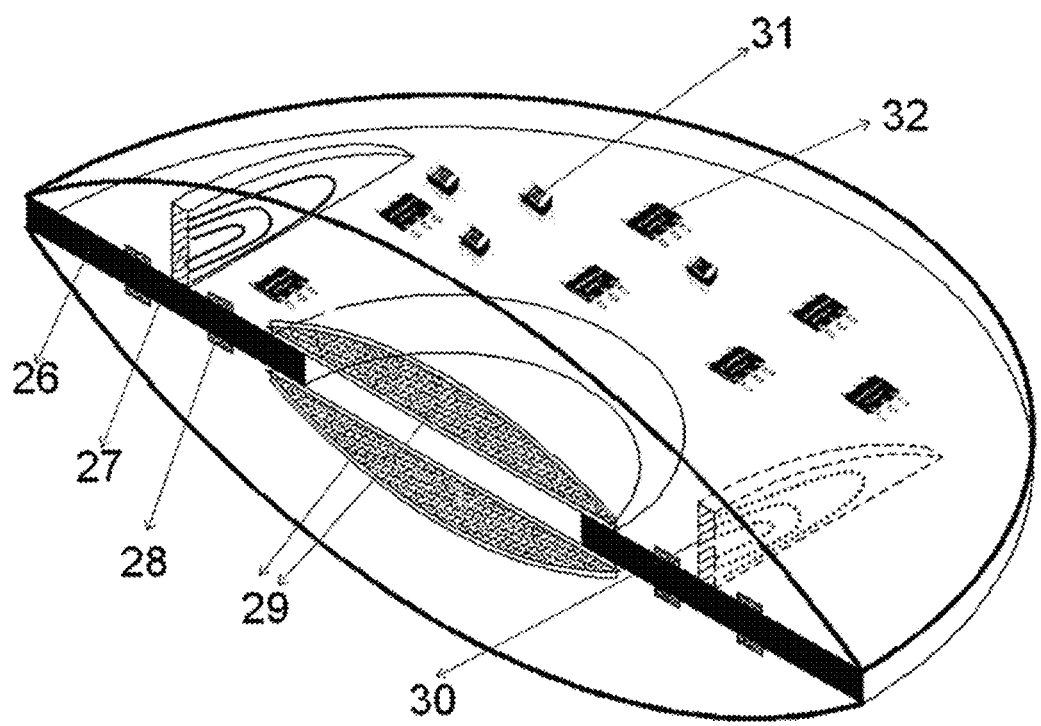
FIG. 3 shows a 3D cross-sectional schematic view of the intraocular lens assembly consisting of a transparent body containing peripheral electronic circuitry in and around the equatorial plane, as well as a coil for detecting the marker distance, where [26] is a Printed Circuit Board (PCB) or Si wafer substrate tor mounting electronic components and holding electro-optic device, [27] is the (primary) detection coil for impedance monitoring, [28] represents electronic components for the oscillator, the phase locked loop and liquid crystal steering electronics, [29] is liquid crystal, [30] is an optional secondary detection coil for a dual or differential marker position detection system, [31] represents electronic components for the oscillator, the phase locked loop and liquid crystal steering electronics and [32] represents electronic components for the oscillator, phase locked loop and liquid crystal steering electronics.

FIG. 3 displays a 3D cross-sectional schematic view of the intraocular lens assembly consisting of a transparent body containing peripheral electronic circuitry in and around the equatorial plane, as well as a coil for detecting the marker distance, wherein [26] is a Printed Circuit Board (PCB) or Si wafer substrate for mounting electronic components and holding electro-optic device, [27] is the (primary) detection coil for impedance monitoring, [28] represents electronic components for the oscillator, the phase locked loop and liquid crystal steering electronics, [29] is liquid crystal, [30] is an optional secondary detection coil for a dual or differential marker position detection system, [31] represents electronic components for the oscillator, the phase locked loop and liquid crystal steering electronics and [32] represents electronic components for the oscillator, phase locked loop and liquid crystal steering electronics. The optical part consists of two liquid crystal based lenses (A and B) placed in series in the optical pathway and embedded in a transparent durable and biocompatible material. The static liquid crystal alignment of lens A is so that changes of the AC voltage $V_{AC}$ over the ITO electrodes affect the refractive index for one polarization component (say horizontal), while they do not affect the refractive index of the perpendicular polarization component (say vertical). The static liquid crystal alignment of lens B is so that changes of the AC voltage over the ITO electrodes affect the refractive index for the vertical polarization component, while they do not affect the refractive index of the perpendicular horizontal polarization component. Both lenses are configured to set synchronously, so that they equally affect all polarization components of the incoming light. For each lens, the changes in liquid crystal alignment lead to a change in refractive index mismatch between the spherical liquid crystal compartment and the surrounding material, and thus to a change in dioptric strength D of the assembly:

$$D = 1/f = (n_2 - n_1)\left(\frac{1}{R_1} - \frac{1}{R_2} + \frac{(n_2 - n_1)\delta}{n_2 R_1 R_2}\right)$$

with f the focal distance of the assembly, $n_2$ the refractive index of the liquid crystal for the given polarization component, $n_1$ the refractive index of the surrounding material, $\delta$ the lens thickness, and $R_1$ and $R_2$ the radii of curvature on the two sides of the lens. The value of $n_2$ depends on the liquid crystal alignment, which can be continuously varied by varying the AC electrode voltage $V_{AC}$ (e-g-square wave of 100 Hz frequency; not DC in order to void ionic currents and electrode polarization effects). $V_{AC}$ is set on the basis of the marker distance monitored by the detection circuitry.

Figure 4:
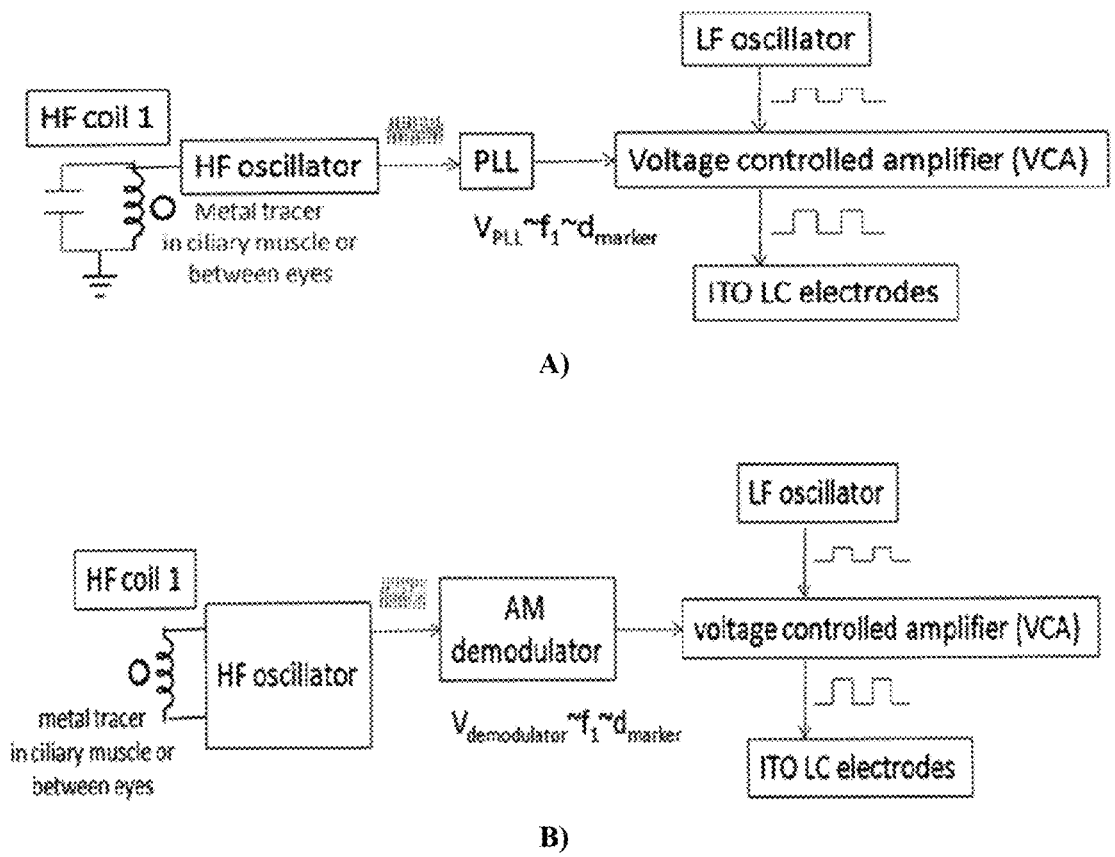
FIG. 4(a) is an electronic circuit to convert the value of L into a control voltage $V_{control}$ in which together with one or more fixed capacitors $9C_1, C_2 \ldots$ ), the coil makes part of an electronic oscillator circuit, the frequency of oscillation being then converted into a voltage by a phase locked loop (PLL) system, with $V_{control} = V_{PLL}$.
FIG. 4(b) is an electronic circuit to convert the value of L into a control voltage in which the value of L determines the amplitude and phase of an oscillation, this amplitude or phase being then converted into a control voltage $V_{control}$ by a demodulator circuit (lock-in amplifier or rectifier).

FIG. 4 is a graphic that displays the distance between the marker and the intraocular assembly, which is representative for the dioptric strength envisaged by the visual cortex (via the state of contraction of the ciliary muscle, or via the rotational position of the eye ball), and which is a parameter determining the electric inductance L of the coil (or the magnetic field and Hall voltage of the Hall probe, in case of a Hall sensor arrangement), (a) FM (de)modulation. One way to convert the value of L into a control voltage $V_{control}$ for the electro-optic part is the following. Together with one or more fixed capacitors ($C_1, C_2, \ldots$), the coil makes part of an electronic oscillator circuit, whose oscillation frequency, is e.g, given by;

$$f_1 = \frac{1}{2\pi\sqrt{LC_1}}$$

for a passive resonator $$f_1 = \frac{1}{2\pi\sqrt{L\frac{C_1 C_2}{C_1 + C_2}}}$$

in a Colpitts oscillator configuration. The frequency of oscillation is then converted into a voltage by a phase locked loop (PLL) system. In this case $V_{control}=V_{PLL}$, (b) AM (de)modulation. A second way to convert the value of L into a control voltage is an electronic circuit in which the value of L determines the amplitude and phase of an oscillation. This amplitude or phase is then converted into a control voltage $V_{control}$ by a demodulator circuit (lock-in amplifier or rectifier).

Both in configurations (a) and (b) in FIG. 4, the control voltage controls the amplification of a voltage controlled amplifier, which sends an AC voltage $V_{AC}$ (e.g. $V_{AC,pp}$ 5 Volt, 100 Hz) to the transparent [e.g. indium tin oxide (ITO)] electrodes over the liquid crystal that fills the electro-optic lens. The change of alignment of the liquid crystal that is induced by $V_{AC}$ results in a proportional change of dioptric strength of the electro-optic lens.

Figure 5A:
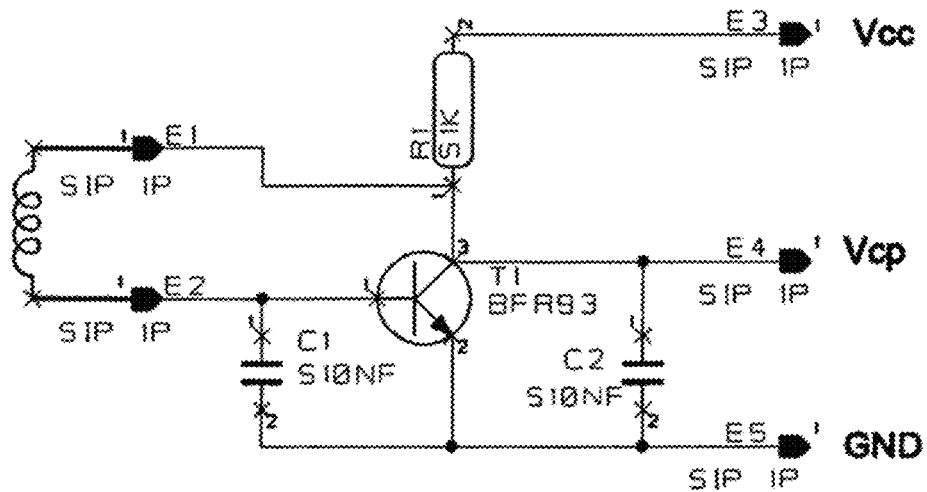
FIG. 5(a) shows an electronic circuit of a Colpitts oscillator with two capacitors and $C_1 = C_2 = 10$ nF.
Figure 5B:
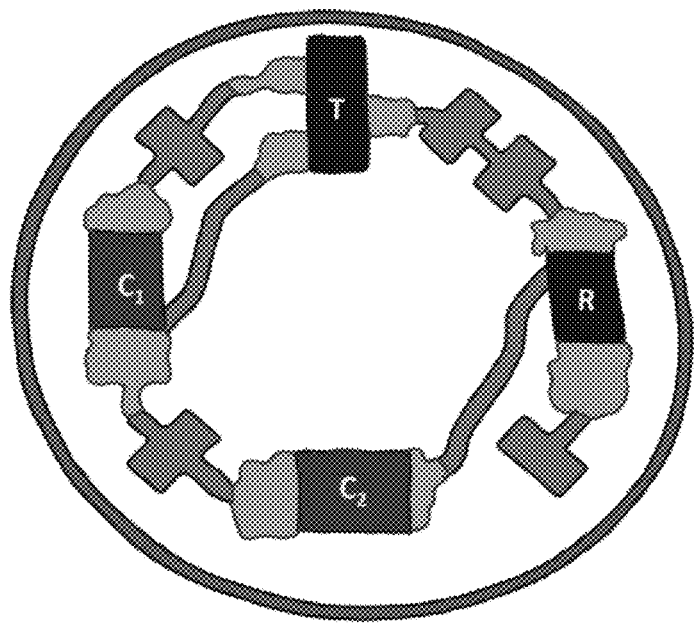
FIG. 5(b) is an example of a Colpitts oscillator, with the two capacitors and the transistor, realized in surface mount technology.
Figure 5C:
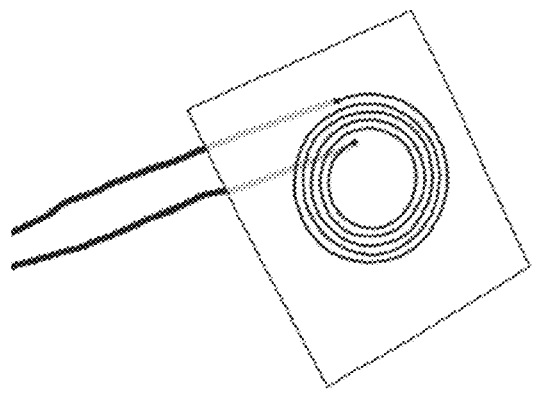
FIG. 5(c) shows the detection coil on the backside of the Colpitts oscillator.

FIG. 5 displays (a) electronic circuit of a Colpitts oscillator with two capacitors and $C_1=C_2=10$ nF, (b) an example of a Colpitts oscillator, with the two capacitors and the transistor, realized in surface mount technology. The empty space in the middle can be used to place the electro-optic part of the bionic eye lens device. The remaining space and backside can hold the detection coil (e.g. (c)), the phase locked loop (PLL) including the voltage controlled oscillator (VCO) electronics, the power supply circuitry, and the liquid crystal alignment control circuitry.

Figure 6A:
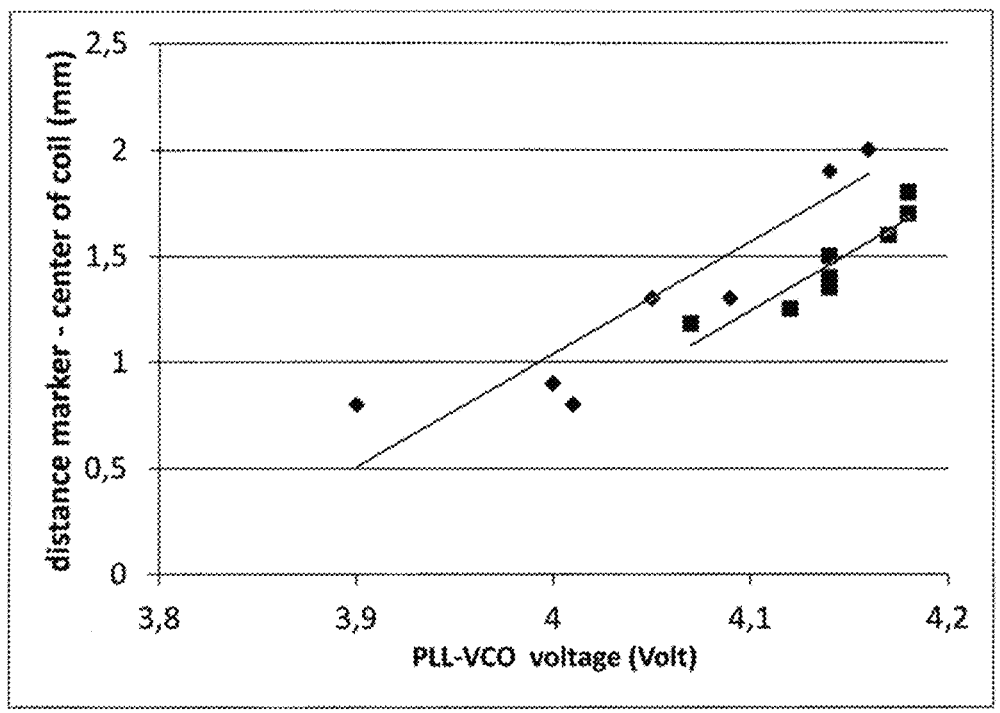
FIG. 6(a) shows a calibration graph in which the distance of marker to center of coil is plotted against PLL-VCO voltage.
Figure 6B:
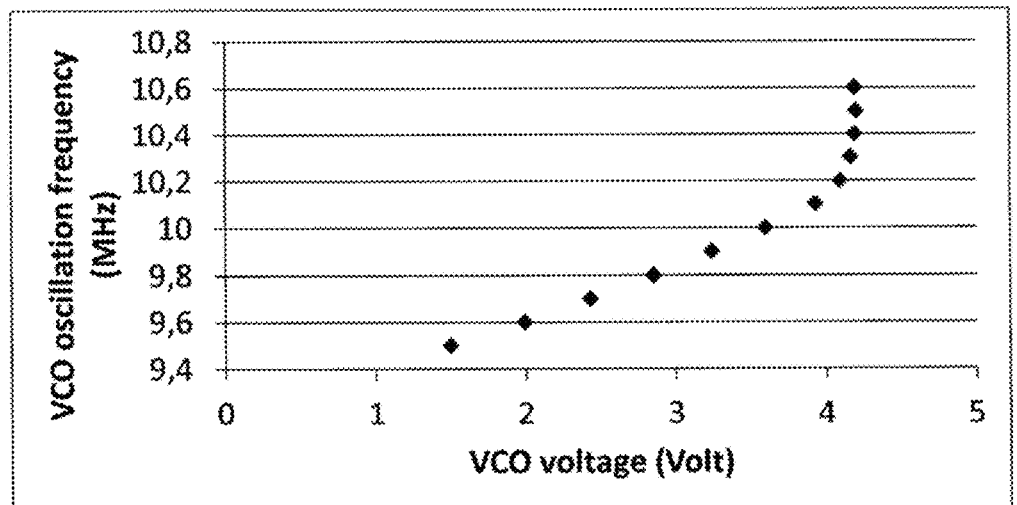
FIG. 6(b) shows a calibration graph in which VCO oscillation frequency is plotted against VCO voltage.

FIG. 6 in graph (a) shows how, for two choices of metal marker objects (a couple of mm in size) in the vicinity of the coil, near to the coil axis, the PLL-VCO voltage and the marker distance are proportional, so that the distance can be derived from the PLL-VCO voltage. To a linear approximation, the PLL-VCO voltage changes with 0.15 Volt/mm. Calibration graph (b) shows the relation between the VCO frequency and VCO voltage. In the linear part of the calibration curve, the VCO frequency changes with 0.5 MHz per 2 Volt. This dependence can be modified by adjusting the electronic VCO parameters. From both calibrations it can be concluded that for the chosen parameters, to a linear approximation, the VCO frequency changes with 75 kHz per mm change in the marker distance, in the case of a marker placed in the ciliary muscle the marker movements due to changes in state of contraction of the ciliary muscle are of the order of (sub-)mm, the distance d between the marker and the coil, which is part of an oscillator circuit in the intra-ocular assembly, determines the inductance L of the coil, and thus the oscillation frequency. The capacitors of the used Colpitts oscillator circuit were $C_1=C_2=10$ nF. In the configuration with a phase locked loop (PLL circuit), the voltage controlled oscillator (VCO) frequency remains locked equal to the oscillator frequency $f_1$; with a response time of typically 1 ms (between 0.1 ms and 50 ms), which is sufficiently fast to the follow changes of d that are controlled by the visual cortex.

Figure 7:
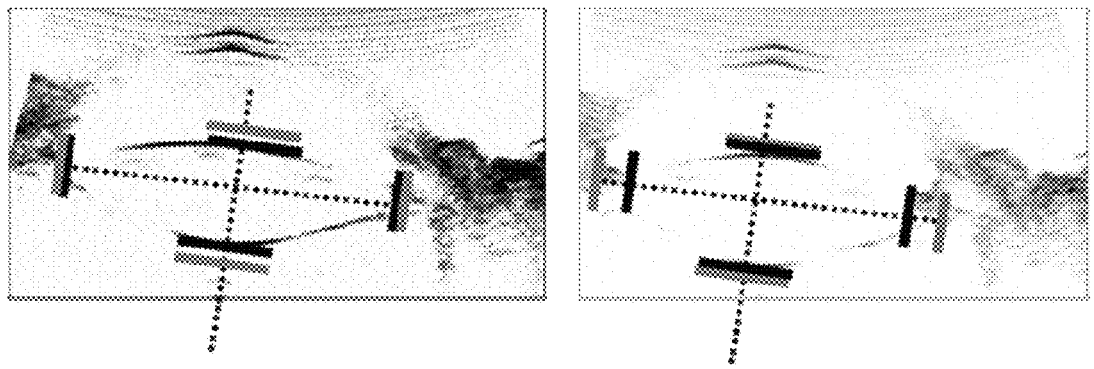
FIG. 7 shows the motion of the ciliary muscle while a person's eye is focusing on two different distances: in the left image, the ciliary muscle is stretching the natural eye lens so that, in the case of a bionic eye lens assembly with fixed shape and position, the marker would be further from the detection coil; and in the right image the ciliary muscle has radially moved towards the center, thus releasing the natural lens, so that it becomes more curved and thus gets a larger dioptric strength.

The images in FIG. 7 depict the motion of the ciliary muscle while a person's eye is focusing on two different distances. In the left image, the ciliary muscle is stretching the natural eye lens so that, in the case of a bionic eye lens assembly with fixed shape and position, the marker would be further from the detection coil. In the right image the ciliary muscle has radially moved towards the center, thus releasing the natural lens, so that it becomes more curved and thus gets a larger dioptric strength. In the case of a bionic eye lens with a fixed position and shape, the marker would here be closer to the detection coil. The motion of the ciliary muscle is about 15% of the natural lens diameter, which would lead to a distance change between the marker and the coil of about 1 mm. In one of the configurations, the feedback mechanism to keep an object in focus by appropriately adjusting the dioptric strength of the intra-optic lens assembly is based on visual cortex controlled changes in the state of contraction of the ciliary muscle, which result in a change of the distance between the marker in the ciliary muscle, and the bionic eye lens assembly.

Figure 8A:
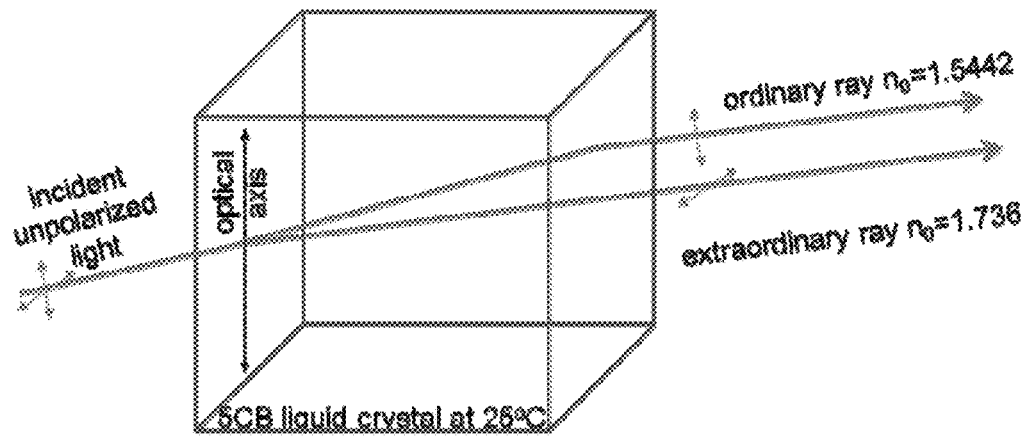
FIG. 8(a) demonstrates the optical anisotropy of a 5CB liquid crystal.
Figure 8B:
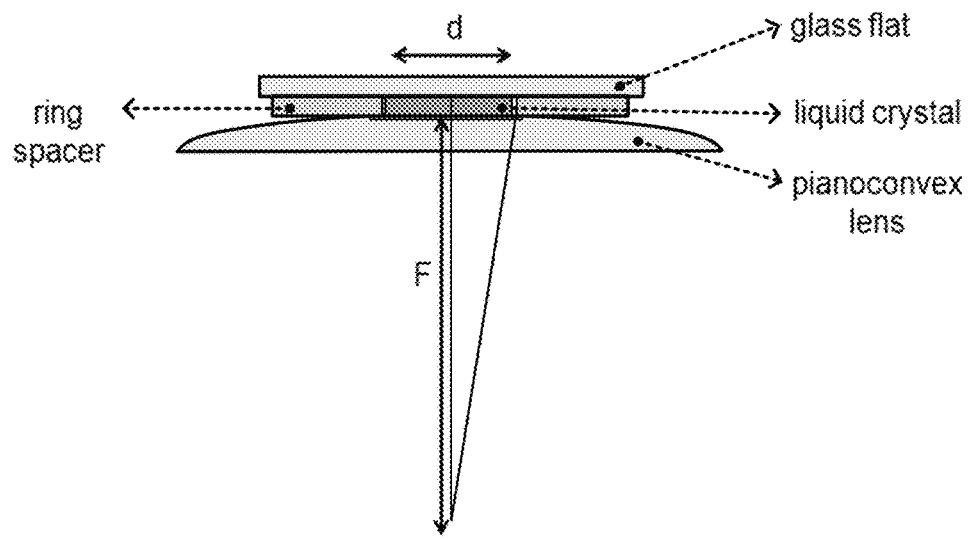
FIG. 8(b) provides the cross section of the lens geometry, where [22] is the ring spaces, [23] is the glass flat, [24] is the liquid crystal and [25] is the pianoconvex lens FIG. 8(c) provides a top view of the circular lens geometry, where [22] is the ring spaces, [23] is the glass flat, [24] is the liquid crystal and [25] is the pianoconvex lens.
Figure 8C:
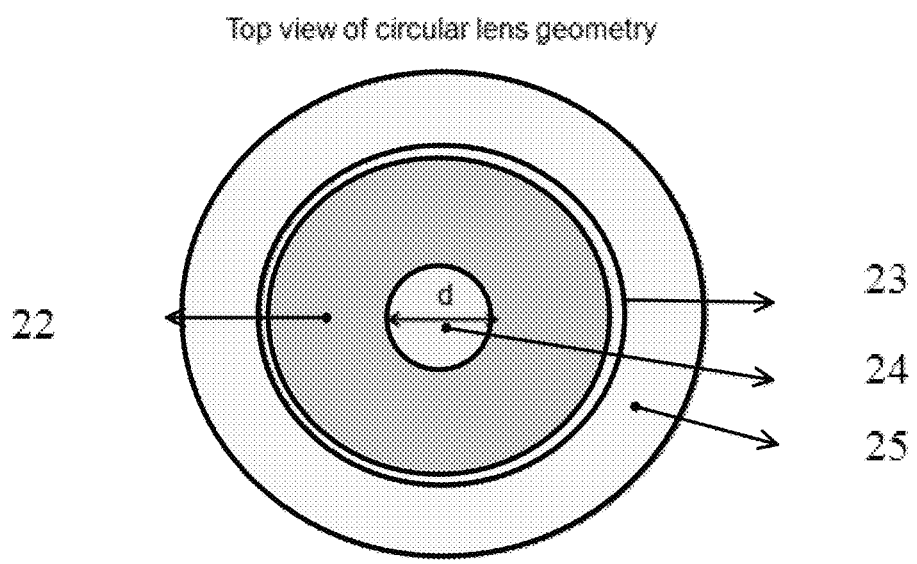

FIG. 8(a) demonstrates the optical anisotropy of a 5CB liquid crystal. FIG. 8(b) provides the cross section of the lens geometry, whereby [22] is the ring spaces, [23] is the glass flat, [24] is the liquid crystal and [25] is the pianoconvex lens FIG. 8(c) provides a top view of the circular lens geometry, whereby [22] is the ring spaces, [23] is the glass flat, [24] is the liquid crystal and [25] is the pianoconvex lens. In a conceptual test assembly pentylcyanobiphenyl (5CB) liquid crystal was used between a BK7 glass flat and the convex-surface of a 1000 mm BK7 piano-convex lens, acting as an electro-optic lens. The opposite lens and flat surfaces in contact with the liquid crystal were coated with indium tin oxide (ITO) electrodes, and with rubbed polyimide for planar alignment. In the absence of an electric field the refractive index of 5CB is about $n//=1.736$ for the extraordinary ray, i.e. the polarization component of incident-light (wavelength 515 nm) parallel with the nematic director (in the rubbing direction used during the polyimide rubbing alignment treatment); the refractive index for the polarization component of incident light perpendicular to the nematic director, i.e. for the ordinary ray, is $n_\perp=1.544$. With electric field applied over the electrodes, both polarization components of incident light (along the normal axis of the assembly), propagate according to $n_\perp=1.544$. For light incident along the axis normal to the assembly, the applied voltage thus has no effect on the polarization component of the incident light that is perpendicular to the nematic director. On the other hand, for the complementary polarization component, parallel with the nematic director, the applied voltage can gradually change the effective refractive index from, (maximum electric field applied), for incident light of 515 nm wavelength the refractive index of BK7 is $n_{BK7}=1.52$. Inserting these values in the approximated lens formula, for small lens thickness δ.

$$D = 1/f = (n_2 - n_1)\left(\frac{1}{R}\right)$$

This gives tor the convex lens used with $f_{air}=1000$ mm in air, and thus $R=(n_{BK7} \ldots 1)\eta=(1.52-1)\ 1000\ \text{mm}=520\ \text{mm}$:

$$D = 1/f = (n_{LC} - n_{BK7})\left(\frac{1}{R}\right) = \frac{n_{BK7} - n_{LC}}{n_{BK7} - 1}\frac{1}{f}$$

with $n_{LC}$ varying between $n//$ and $n_\perp$ for the extraordinary polarization component, and remaining fixed to $n_\perp$ for the ordinary polarization component. Thus for the extraordinary polarization component the magnitude of the dioptric strength varies between 0.05 and 0.4. For a stronger variation, a more curved lens surface can be used, in order to decrease $f$. By placing two of these lenses in series, with mutually perpendicular nematic director orientations, the dioptric strength for both polarization components can be controlled by varying both respective electrode voltages.

Eye implantable unit of an intraocular device, or intraocular implant system

A first aspect of the present invention is the realization of an eye implantable unit of an intraocular device or intraocular implant system with an electro-optic self-adaptive artificial lens which comprises 1) signal conversion mechanism that converts inductively detected ciliary muscle contraction into an appropriate change of dioptric strength of 2) an electro-optic artificial lens assembly comprising a transparent liquid-crystal display, consisting of a liquid crystal confined between transparent uniform electrode coated lenses, with a refractive index that is changed if an AC voltage, electronically controlled on the basis of the contraction state of the ciliary muscle, is applied between the electrodes so that the dioptric strength of the assembly is changed in a similar way as a natural mechanically modified eye lens would due for the same ciliary muscle contraction, thus making possible a feedback system where on the basis of the sharpness of the image processed in the visual cortex, via the ciliary muscle signal, the dioptric strength of the electro-optic eye lens assembly is continuously adapted.

A second aspect of the present invention is the realization of an eye implantable unit of an intraocular device or of an intraocular implant system comprises 1) an electro-optic self-adaptive artificial lens assembly comprising at least one electrode and a refractive liquid-crystal display assembly with changeable refractive index and 2) a signal conversion mechanism adapted to convert ciliary muscle contraction into a proportional change of voltage signal adapted by the voltage change on the electrode to induce a change in dioptric power or change of dioptric strength of said artificial lens.

The eye implantable unit of the above aspects, can comprise a lens assembly, is a dual lens assembly with intra-optic lenses electronically controllable liquid crystal sandwiched between and aligned with transparent electrode-coated curved surfaces forming a concave lens shape where the refractive power of intra-optic lens is made polarization independent by optically processing two orthogonal polarization components of the light in series, thus proportionally retracting all polarization components of the incident light. This eye implantable unit can be chargeable via a transformer circuit between a receiving coil in the intra-optic lens and a transmitting coil in front of the eye suitable for wireless receiving energy.

In the eye implantable unit of the above aspects, the liquid crystal layer can be sandwiched between two flat transparent (e.g. glass or transparent polymer) slides that are provided by an electrode matrix (composite pattern of metal and indium tin oxide (ITO) electrodes) that can be holographically programmed to act as a lens with programmable dioptric power and a layer of coating to insure planar alignment (nematic director tangential to the interface) of a liquid crystal without voltage applied on the electrodes. The liquid crystal layer can be a liquid crystal E7. Furthermore one of the slides can be provided with a uniform electrode pattern. Moreover the other slide can be covered with a uniform indium tin oxide (ITO) electrode or other optically transparent and electrically conductive electrode and has a piano-concave shape.

In a particular embodiment the eye implantable unit of any of the above aspects has the liquid crystal sandwiched between the double-flat slide and the concave part of the piano-concave slide. In a particular embodiment the eye implantable unit of any of the embodiments here above described the eye-implantable unit has the refractive index mismatch for a given polarization of the incident light between the slide material and the liquid crystal matrix changed by the voltage applied on it.

In such eye implantable unit of any of the above aspects the dioptric power of the electro-optic assembly, and thus the focal point of the eye containing the intra-optic assembly, is in a particular embodiment under electronic control.

In any of the above aspects particular features are possible. The lens is in a particular embodiment is a lens assembly of two plane parallel lenses (having opposite surfaces exactly plane and parallel) with a radial refractive index gradient, depending on optical thickness of the liquid crystal (LC) layer between two opposite lenses the focal distance of this assembly will vary. In yet another embodiment the lens is a curved lens with a patterned hole electrode tor an electrical field gradient. Furthermore an assembly of intra-optic lens with controllable dioptry comprises a LC sandwiched between two flat slides one having a uniform electrode, and the other one having a patterned electrode consisting of concentric circles with a radial line density varying so that the local electric field decreases with increasing distance from the centre or vice versa can be comprised in such an implantable eye unit.

In any of the above aspects on the eye implantable unit in a further embodiment the signal conversion mechanism to perform the conversion of the ciliary muscle contraction state changes into a proportional change of voltage signal for steering the intra-optical lens and thus its dioptric strength comprises the interacting elements a) an electromagnetic marker tag attached to the ciliary muscle and a lens controller which comprises b) an electronic circuit and c) a coil positioned on the lens, whereby a steering signal proportional to the state of the ciliary muscle is electronically and remotely derived from the inductance of the coil generated by the electromagnetic tag coil interaction and recovering of the information content of the inductance by the electronic demodulation circuitry to have a signal that is proportional to the position of the ciliary muscle marker tag.

Yet another embodiment of the above aspects of present invention is the eye implantable unit of any of the previous embodiments, whereby the eye implantable unit comprises a steering system for eye accommodation for electronically and remotely deriving a lens steering system based on the state of the ciliary muscle the steering system comprising 1) an electromagnetic marker tag (for instance ferromagnetic or metallic nanoparticles dispersed in the ciliary muscle tissue, a piece of metal, or a biocompatible piece of material containing an inductive coil element that can result in mutual inductance effects with the detection coil of an LC oscillator on the intra-optic lens assembly) on said the ciliary muscle, 2) at least one coil positioned on the lens for sensing changes of induction related to positional changes of the marker attached to the ciliary muscle and 3) an electronic demodulation circuitry, preferably a FM demodulation circuitry, on the lens, for extracting the original information-bearing signal from the inductance change in the circuit used for controlling the intra-optic lens.

Yet another embodiment of above aspects of the present invention is the eye implantable unit of any of the above embodiments, whereby the eye implantable unit comprises a steering system for eye accommodation for electronically and remotely deriving a lens steering system based on the state of the ciliary muscle the steering system comprising 1) a magnetic marker tag (for instance a metal particle, or metallic or ferromagnetic nanoparticles) on said the ciliary muscle, 2) at least one Hall sensor that detects the position of the ciliary muscle marker tag and 3) an electronic demodulation circuitry for extracting the original information-bearing signal from the inductive changes.

Yet another embodiment of present invention is the eye implantable unit of any of the above embodiments, whereby the signal conversion mechanism to perform the conversion of the ciliary muscle contraction state changes into a proportional change of the voltage signal for steering the intra-optical lens and thus its dioptric strength comprises the interacting elements a) an electromagnetic marker tag attached to the ciliary muscle, b) an electronic circuit and c) a Hall sensor, whereby a steering signal proportional to the state of the ciliary muscle is electronically and remotely derived from the inductance of the coil generated by the magnetic tag with Hall sensor interaction and recovering of the information content of the inductance by the electronic-demodulation circuitry to have a signal that is proportional to the position of the muscle marker tag. The electronic circuit can be an electronic (FM) demodulation circuitry on the lens, the electronic circuit can be an analogue circuit and/or the electronic circuit can be a digital circuit.

Yet another embodiment of present invention is the eye implantable unit of any of the above embodiments, whereby the electromagnetic marker tag attached to the ciliary muscle is one or more ferromagnetic tracer particles.

Yet another embodiment of present invention is the eye implantable unit of any of the above embodiments, wherein the electromagnetic marker tag attached to the ciliary muscle is one or more metallic tracer particles.

Yet another embodiment of present invention is the eye implantable unit of any of the above embodiments, wherein the frequency or amplitude of an electronic circuit is influenced by a marker tag in the ciliary muscle.

Another embodiment of present invention concerns an eye implantable unit of any of the above embodiments whereby the signal transfer from the ciliary muscle to the lens controller is by a non-contact mechanism, in which the changes of the state, i.e. the radial contraction distance, of the ciliary muscle, containing a ferromagnetic tracer particle attached to the ciliary muscle, are monitored by the induced electric inductance changes in a pick-up coil placed on the intra-optic lens or in a Hall sensor to translate a particular design, axial or radial or combined motions of the tracer particle are translated into proportional inductance changes. This circuit can recover the information content of the modulated voltage of the coil or the Hall sensor and in a particular embodiment the circuit recovers the information content of the modulated electric impedance of the coil, which can be detected as amplitude modulations (AM detection) or frequency modulations (FM detection) of the oscillator built around the coil.

Yet another embodiment of present invention is the eye implantable unit of any of the above embodiments, comprising a first lens which acts on horizontal light polarization component normal to the cross-section and a second lens which acts on the vertical light polarization components.

Yet another embodiment of present invention is the eye implantable unit of any of the above embodiments, comprising a first high frequency coil, which acts as the secondary coil in a transformer containing also the external AC power supply coil and a second high frequency coil which acts as an inductive sensor of the position of the magnetic or metallic tag, for instance one or more magnetic or metallic particles, or a tag containing a coil in the ciliary muscle Yet another embodiment of present invention is the eye implantable unit of any of the above embodiments, comprising a first high frequency coil which acts as the secondary coil in a transformer containing also the external AC power supply coil and a second high frequency coil which acts as an inductive sensor of the position of the magnetic tag, of the magnetic or metallic tag, for instance one or more magnetic or metallic particles, or a tag containing a coil, placed centrally between the eyes for sensing the angular orientation of the eye balls, which is a measure for the distance of the object the person wants to focus on. Yet another embodiment of present invention is the eye implantable unit of any of the previous embodiments, configured to function with an external energy source.

Furthermore an embodiment of present invention concerns a totally implantable eye implant system having an implantable unit of any of the above embodiments. This implantable eye implant system can be a self-adapting system. The implantable eye implant system furthermore can comprise an intra-ocular lens with electro-optically controlled refractive power.

Yet another embodiment of present invention is the eye implantable unit of any of the above embodiments, which is an intra-ocular and biocompatible miniaturized electro-optic device. Yet another embodiment of present invention is the eye implantable unit of any of the previous embodiments or a device comprising such unit which is wireless connectable to an energy providing means (energizing device) to supply of energy from a device out of the body Yet another embodiment of present invention is device of any of the previous embodiments, which is wireless connectable to an energy providing means (energizing device) which comprises a (near infrared, invisible) light transmitter in front of the eye to a solar cell on the eye lens and by inductive electromagnetic transmission of AC whereby the energizing device is coil in front of or around the eye to a coil on the intraocular lens to provide electromagnetic energy. The wireless energy supply system can also used to exchange information between the intra-optic lens circuitry and a controller outside the body, via FM or AM modulation of electromagnetic waves sent to or from the intra-optic lens circuitry.

The present invention also provides the eye implantable unit according to the first or second aspect of the present invention, comprising a lens assembly whereby the lens assembly is a dual lens assembly with intra-optic lenses electronically controllable liquid crystal sandwiched between and aligned with transparent electrode coated curved surfaces forming a concave lens shape where the refractive power of intra-optic lens is made polarization independent by optically processing two orthogonal polarization components of the light in series, thus proportionally refracting all polarization components of the incident light. Moreover the invention also provides an eye implantable unit according to this first embodiment which is chargeable via a transformer circuit between a receiving coil in the intra-optic lens and a transmitting coil in front of the eye suitable for wireless receiving energy.

In additional, the present invention concerns the eye implantable unit according to the first or second aspect of the present invention or according to any one of the above variants of the first or second aspects of the present invention, whereby the liquid crystal layer is sandwiched between two flat transparent (e.g. glass or transparent polymer) slides that are provided by a holographically programmable electrode matrix (composite pattern of metal and indium tin oxide (ITO) electrodes) and a layer of coating to insure planar alignment (nematic director tangential to the interface) of a liquid crystal without voltage applied on the electrodes. The other slide can be covered with a uniform indium tin oxide (ITO) or other optically transparent and electrically conductive electrode and has a piano-concave shape.

In additional, the present invention concerns the eye implantable unit according to the first or second aspect of the present invention or according to any one of the above variants of the first or second aspects of the present invention, whereby the liquid crystal layer is liquid crystal E7. In additional, the present invention concerns the eye implantable unit according to this first embodiment and to any one of the previous variants of this first embodiment, whereby one of the slides is provided with a uniform electrode pattern. In additional, the present invention concerns the eye implantable unit according to this first embodiment and to any one of the previous variants of this first embodiment, whereby the liquid crystal is sandwiched between the double-flat slide and the concave part of the piano-concave slide.

The invention also provides the eye implantable unit according to the first or second aspect of the present invention or according to any one of the above variants of the first or second aspects of the present invention, whereby the refractive index mismatch for a given polarization of the incident light between the slide material and the liquid crystal matrix is changed by the voltage applied on it; Or whereby the dioptric power of the electro-optic assembly, and thus focal point of the eye containing the intra-optic assembly, is under electronic control; Or whereby the lens is a lens assembly of two plane parallel lenses (having opposite surfaces exactly plane and parallel) with a radial refractive index gradient, depending on optical thickness of the de liquid crystal (LC) layer between two opposite lenses the focal distance of this assembly will vary; Or whereby the lens is a curved lens with a patterned hole electrode for obtaining an electrical field gradient; Or whereby assembly of intra-optic lens with controllable dioptry comprises a LC sandwiched between two flat slides has a uniform electrode, and the other one a patterned electrode consisting of concentric circles with a radial line density varying so that the local electric field decreases with increasing distance from the center or vice versa.

In particular, the present invention provides the eye implantable unit according to the first or second aspect of the present invention or according to any one of the above variants of the first or second aspects of the present invention, whereby the signal conversion mechanism to perform the conversion of the ciliary muscle contraction state changes into a proportional change of voltage signal for steering the intra-optical lens and thus its dioptric strength comprises the interacting elements a) an electromagnetic marker tag (for instance metallic or magnetic particle(s) or coil) attached to the ciliary muscle and a lens controller which comprises b) an electronic circuit and c) a coil positioned on the lens, whereby a steering signal proportional to the state of the ciliary muscle is electronically and remotely derived from the inductance change of the coil induced by positional changes of the electromagnetic tag-coil, interaction and recovering of the information content of the inductance by the electronic demodulation circuitry to have a signal that is proportional to the position of the muscle marker tag.

The present invention also provides the eye implantable unit according to the first or second aspect of the present invention or according to any one of the above variants of the first or second aspects of the present invention, wherein the eye implantable unit comprises a steering system for eye accommodation for electronically and remotely deriving a lens steering system based on the state of the ciliary muscle the steering system comprising 1) an electromagnetic marker tag (for instance metallic or magnetic particle(s) or coil) on said the ciliary muscle, 2) at least one coil positioned on the lens for generating an inductive change on a changed state of the ciliary muscle and 3) an electronic oscillator demodulation circuitry, preferably a FM demodulation circuitry, on the lens, for extracting the original information-bearing signal from the inductance change of the oscillator coil in the circuit used for controlling the intra-optic lens.

The present invention also provides the eye implantable unit according to the first or second aspect of the present invention or according to any one of the above variants of the first or second aspects of the present invention, whereby the eye implantable unit comprises a steering system for eye accommodation for electronically and remotely deriving a lens steering system based on the state of the ciliary muscle the steering system comprising 1) an electromagnetic marker tag (for magnetic particle(s) or coil) on the said ciliary muscle, 2) at least one Hall sensor detects the position of the ciliary muscle marker tag and 3) an electronic conversion circuitry, for extracting the original information-bearing signal from the Hall voltage changes related with the magnetic particles position.

Furthermore the present invention also provides the eye implantable unit according to the first or second aspect of the present invention or according to any one of the above variants of the first or second aspects of the present invention, whereby the signal conversion mechanism to perform the conversion of the ciliary muscle contraction state changes into a proportional change of voltage signal for steering the intra-optical lens and thus its dioptric strength comprises the interacting elements a) an electromagnetic marker tag attached to the ciliary muscle, b) an electronic circuit and c) a Hall sensor, whereby a steering signal proportional to the state of the ciliary muscle is electronically and remotely derived from the Hall voltage change generated, by the magnetic tag with magnetic interaction and recovering of the information content to have a signal that is proportional to the position of the muscle marker tag. In any of these previous embodiments the electronic circuit can be an electronic conversion circuitry on the lens. Moreover the electronic circuit can be an analogue and the electronic circuit can be a digital circuitry. Furthermore in any of these previous embodiments the electromagnetic marker tag attached to the ciliary muscle can be ferromagnetic tracer particles and the electromagnetic marker tag attached to the ciliary muscle can be one or more metallic tracer particles. The electromagnetic marker tag can also be a coil or other inductive element. Furthermore the frequency or amplitude of an electronic circuit can be influenced by a marker tag in the ciliary muscle. Hereby the signal transfer from the ciliary muscle to the lens controller can be by a non-contact mechanism, in which the changes of the state, i.e. the radial contraction distance, of the ciliary muscle, containing a ferromagnetic or metallic tracer particle attached to it are monitored by the induced electric inductance changes in a pick-up coil placed on the intra-optic lens or in a Hall sensor to translate a particular design, radial motions of the tracer particle are translated into proportional inductance or respectively Hall voltage changes. Hereby the circuit can recover the information content of the FM or AM modulated oscillation of the coil or the Hall sensors. Hereby the circuit can recover the information content of the modulated electric impedance of the coil which can be detected as amplitude modulations (AM detection) or frequency modulations (FM detection) of the oscillator built around the coil.

Furthermore, the eye implantable unit according to the first or second aspect of the present invention or according to any one of the above variants of the first or second aspects of the present invention, in a particular embodiment comprises a first lens which acts on horizontal light polarization component normal to the cross-section and a second lens which acts on the vertical light polarization components.

The eye implantable unit according to the first or second aspect of the present invention or according to any one of the above variants of the first or second aspects of the present invention, comprising a first high frequency coil which acts as the secondary coil in a transformer containing also the external AC power supply coil and a second high frequency coil, which acts as an inductive sensor of the magnetic tag, for instance metallic or magnetic particle(s) or coil in the ciliary muscle. This eye implantable unit of present invention can comprise a first high frequency coil which acts as the secondary coil in a transformer containing also the external AC power supply coil and a second high frequency coil which acts as an inductive sensor of the magnetic tag, for instance metallic or magnetic particle(s) or coil, placed centrally between the eyes for remotely sensing the angular orientation of the eye balls, which is a measure for the distance of the object the person wants to focus on. This implantable unit can further be configured to function with an external energy source.

A totally implantable eye implant system can comprise the implantable unit the previous first embodiment or according to any one of the previous variants of this first embodiments. This implantable eye implant system can be a self-adapting system. Such implantable eye implant system can comprises an intraocular lens with electro-optically controlled refractive power. Moreover such implantable eye implant system according to present invention can be an intra-ocular and biocompatible miniaturized electro-optic device.

Electro-Optical Implant Assembly

In a third embodiment of the present invention, an electro-optical implant assembly is realized, the implant assembly comprising 1) an electronic detector system or device which has a motion detector element and a 2) an electro-optic artificial lens assembly and further comprising (3) a marker element having a marker or markers adapted to induce electric impedance variation on the motion detector element in relation to the positional modification or in relation to the spatiotemporal features of said marker element versus detector system to convert the electric impedance variation into a change of dioptric strength of the electro-optic artificial lens assembly is a particular second embodiment of present invention. In this electro-optical implant the motion detector element can comprise at least one inductive defector element and this inductive detector element can be or can comprise any one of the following elements: an inductive coil or a wired inductive material or a deposited metal structure or a printed circuit board or this inductive detector element can be or can comprise an inductive coil which is electronically monitored by an electronic circuit. Furthermore the electronic circuit can be an amplitude detection circuit or a frequency detection circuit, in yet another embodiment of present invention concerns this third aspect of the present invention or variants thereof as here above described have a motion detector element winch comprises at least one Hall sensor (magnetic signal).

The electro-optical implant assembly according to the third aspect of the present invention and the adaptations or variations thereon here above described, can comprise a signal conversion mechanism adapted to convert the electric impedance variation into a change of dioptric strength of the electro-optic artificial lens assembly.

Yet an embodiment of present invention concerns an electro-optical implant assembly according to the third aspect of the present invention and the adaptations or variations thereon here above described, whereby the electro-optic artificial lens assembly comprising a refractive liquid-crystal display assembly with changeable refractive index and thus dioptric power if voltage is applied on the electrodes.

Yet another embodiment of present invention concerns an electro-optical implant assembly according to the third aspect of the present invention and the adaptations or variations thereon here above described, whereby the detector system is electrically or electronically connected with the electro-optic artificial lens assembly so that an electronic signal or a time-varying voltage or current that conveys information of said spatiotemporal variation of marker versus detector system is translated to a change of dioptric strength of said electro-optic artificial lens assembly.

Yet another embodiment of present invention concerns an electro-optical implant assembly according to the third aspect of the present invention and the adaptations or variations thereon here above described, whereby movement of the marker element modifies an electromagnetic field or oscillations in the electromagnetic field.

Yet another embodiment of present invention concerns an electro-optical implant assembly according to the third aspect of the present invention and the adaptations or variations thereon here above described, comprising an electro-optic self-adaptive artificial lens.

Yet another embodiment of present invention concerns an electro-optical implant assembly according to the third aspect of the present invention and the adaptations or variations thereon here above described, whereby the marker element is electromagnetically detectable. Yet another embodiment of present invention concerns an electro-optical implant assembly according to any one of the previous second embodiment and the adaptations or variations thereon here above described, whereby the marker element is one of the following elements: a paramagnetic element or a ferromagnetic element or an electrically conductive element.

Yet another embodiment of present invention concerns an electro-optical implant assembly according to the third aspect of the present invention and the adaptations or variations thereon here above described, whereby the motion detector element is electronically connected with the marker element to generate a steering signal for refractive power control of the lens assembly which is representative for an optic nerve signal from the visual cortex generated from neuronal processed spatiotemporal features and to change the dioptric strength in order to get a sharp image.

Yet another embodiment of present invention concerns an electro-optical implant assembly according to the third aspect of the present invention and the adaptations or variations thereon here above described, whereby the motion detector is electronically connected with the marker element to generate a time-varying voltage or current in the lens assembly to control the refractive power of the lens whereby the time-varying voltage or current conveys information of the visual cortex or its optical nerve.

Yet another embodiment of present invention concerns an electro-optical implant assembly according to the third aspect of the present invention and the adaptations or variations thereon here above described, whereby the detection of the electronic detection system or detection device is based on the monotonic relation between the marker position, and the electric impedance of an inductive element comprised in a detector system.

A particular embodiment of present invention concerns an electro-optical implant assembly according to the third aspect of the present invention and the adaptations or variations thereon here above described, for use in a surgical treatment of a patient to restore or improve vision sharpness whereby the markers are surgically placed in said a patient so that the markers are comprised in or are on the ciliary muscle, or near to it, in the zonular fiber connection zone between the ciliary muscle and the lens body.

Furthermore the invention in a particular embodiment can concern an electro-optical implant assembly according to the third aspect of the present invention and the adaptations or variations thereon here above described, for use in a surgical treatment of a patient to restore or improve vision sharpness whereby after surgery the electronic detection system, in total or in part or its core, is located in the peripheral zone of the artificial intraoptic lens, preferably out of the transparent zone which transmits the light from the outside world to the retina and whereby the marker or markers are subcutaneously or attached to the skin placed in the region between both eyes, or close to eyes, so that at turning-in of the eye balls towards the central axis in the vision direction the degree of turning-in translated in the degree of impedance variation on the motion detector element.

Furthermore the invention in a particular embodiment can concern an electro-optical implant assembly according to the third aspect of the present invention and the adaptations or variations thereon here above described, for use in a surgical treatment of a patient to restore or improve vision whereby after surgery the one or more markers and/or detection systems are placed in both eyes so that turning-in of the eyes then also is reflected in the relative positions between marks and detection systems and that the derived impedance signals in the electro-optic circuitry controls the dioptric strength of the lens.

Yet another embodiment of present invention concerns the electro-optical implant assembly according to the third aspect of the present invention and the adaptations or variations thereon here above described, comprising a lens assembly whereby the lens assembly is a dual lens assembly with intra-optic lenses electronically controllable liquid crystal sandwiched between and aligned with transparent, electrode coated curved surfaces forming a concave lens shape where the refractive power of intra-optic lens is made polarization independent by optically processing two orthogonal polarization components of the light in series, thus proportionally refracting all polarization components of the incident light.

Medical Devices

A seventh aspect of the present invention is the provision of a medical device of any one of the first, second, third, fourth, fifth and sixth aspects of the present invention for use in a treatment to restore or improve the quality of human vision.

An eighth aspect of the present invention is the provision of a medical device of any one of the first, second, third, fourth, fifth and sixth aspects of the present invention for use in a treatment for achieving automatic sharp vision by the human eye of objects e.g. at distances between 25 cm and more than 10 meters away.

In a particular embodiment of present invention the medical device described here above is wireless connectable to an energy providing means (energizing device) to supply of energy from a device out of the body, for instance the medical device is wirelessly connectable to an energy providing means (energizing device) which comprises a (near infrared, invisible) light transmitter in front of the eye to a solar cell on the eye lens and by inductive electromagnetic transmission of AC whereby the energizing device is a coil in front of or around the eye to a coil on the intraocular lens to provide electromagnetic energy.

Particular and preferred aspects of the invention are set out in the accompanying independent and dependent claims. Features from the dependent claims may be combined with features of the independent claims and with features of other dependent claims as appropriate and not merely as explicitly set out in the claims. Thus, the claims following the detailed description are hereby expressly incorporated into this detailed description, with each claim standing on its own as a separate embodiment of this invention.

EXAMPLES

Example 1

Novel Artificial Lens (A)

The novel artificial lens operates electro-optically and comprises a transparent, refractive liquid-crystal display that is AC voltage controlled in order to generate a lens with desired dioptric power.

A liquid crystal layer is sandwiched between two transparent (e.g. glass or transparent polymer) slides, of which one or both are curved, that are provided by a uniform electrode (indium tin oxide (ITO) electrodes) and a layer of coating to ensure planar alignment (nematic director tangential to the interface) of a liquid crystal without voltage applied on the electrodes. When a voltage is applied on the electrode, the electric field induces locally a change of nematic director towards a more homeotropic alignment (nematic director perpendicular to the interface), thus locally changing the local refractive index for a proper incoming light polarization from a value close to n// (refractive index value for the electric field component of the electromagnetic light wave, and thus the light polarization, parallel to the nematic director) to n (refractive index value for the electric field component of the electromagnetic light wave, and thus the light polarization, perpendicular to the nematic director). E.g. for the commercial liquid crystal E7 (Merck®), $n_{//}$=1.69 and $H_\perp$=1.50. The refractive index of the curved or flat materials sandwiching the liquid crystal can be chosen in order to result in a desired refractive power of the assembly in rest (no voltage applied) and for maximum electric field (maximum voltage applied) conditions. The refractive power of the assembly will then vary between the desired minimum and maximum in a monotonic with increasing or decreasing AC voltage applied on the electrodes. In an alternative to the curved liquid crystal assembly, use can be made of a liquid crystal sandwiched between slides provided with an electrode matrix that can be holographically programmed using Fresnel diffraction theory so as to achieve any desired refractive effect. when the holographic LCD is to act as an amplitude mask acting on the light intensity, then this is achieved by placing crossed polarizers for the incoming and returning beam (reflected or transmitted beam depending on the particular configuration). Due to the polarization dependence of the optical phase changes, the LCD can rotate the polarization of the light, thus, in combination with the crossed polarizers, modify the light intensity according to a programmed matrix pattern. For a holographic LCD display acting as a lens, only optical phase changes are needed.

In an embodiment of the invention, one of the slides is provided with a uniform electrode pattern. The other slide is covered with a uniform indium tin oxide (ITO) electrode, but has a piano-concave shape. The LC is sandwiched between the double-flat slide and the concave part of the piano-concave slide. Both slides are treated to give planar orientation without voltage applied. By choosing the materials for LC and slides, the refractive index mismatch (for a given polarization of the incident light) between the slide material and the LC can be chosen to be zero, positive or negative in the absence of an applied voltage. With a voltage applied, depending on the choice of LC and slide material, the refractive index mismatch can be gradually-changed towards a new value, which can be zero, positive or negative. Clearly, the design is such that the magnitude of the refractive index mismatch (for the given polarization of the incident light) is determining the dioptric power of the novel assembly, with a monotonic relation between the applied voltage and the resulting dioptric strength. As a result, full electronic control over the dioptric power of the electro-optic assembly, and thus focal point of the eye containing the intra-optic assembly, is possible. This approach can thus be used as an electro-optic lens. For a liquid crystal with effective refractive index set to ULC sandwiched between a double-flat and a piano-concave slide (radius of curvature R) with refractive index $n_{slide}$, the dioptric strength D and focal distance are given by:

$$D = \frac{1}{f} = \frac{(n_{slide} - n_{LC})}{R}$$

By plugging in the values for the LC E7 given above, and a typical value for the refractive index of biocompatible slide material $n_{slide}$=1.50 (acryl values vary between 1.47 and 1.55), D can be varied between 0 (for $n_{LC}$=n//=1.50) and 0.19/R (for $n_{LC}$=$n_\perp$=1.69). If the assembly is made with R=0.19/4=0.0475, then the usual dioptric range 0 to 4, needed for full accommodation for focusing on objects at distances between infinity and 25 cm away, is covered.

Note that although the refractive index of liquid crystals is significantly temperature dependent, this poses no problem, since the human body stabilizes the inner eye ball temperature in a narrow range (extreme values: 35° C. and 39.5° C.).

Measures can be taken to minimize effects of spherical and chromatic aberration. Without special measures, to pre-select the polarization, of the incoming light, the design is intrinsically sensitive to the polarization of the incoming light, so that potentially a fraction of the useful light is not appropriately focused, leading to halo or glaring effects.

An embodiment comprising an alternative variant of this concept concerns an assembly of a LC sandwiched between two flat slides, of which one has a uniform electrode, and the other one a patterned electrode consisting of concentric circles with a radial line density varying so that the local electric field decreases with increasing distance from the center (or vice versa). The resulting electric field decrease results in a radially decreasing homeotropic alignment, and thus in optical path changes for the transmitted light that result in a converging (or diverging for the electrode line density increasing with distance from the center) lens action. This assembly is particularly suitable as an intra-optic lens with controllable dioptry.

An embodiment comprising an improved variant, of this concept makes uses of two of the above-described assembles in series, with the respective liquid crystal films aligned in such a way that they act on two respective orthogonal polarization components of the incident light. In this way close to 100% of the incident light is correctly focused onto the retina.

Example 2

Novel Conversion Mechanism (B)

The second part of the invention consists of a specific way to perform the conversion of the ciliary muscle contraction state changes, which are a measure of how the visual cortex wants to change the focal point of the eye, into a proportional change of voltage signal for steering (by means of direct analogue electronics, or via a digital circuitry including additional signal processing and monitoring) the intra-optical lens, and thus its dioptric strength. Electro-myographic signals from the nerves in or towards the ciliary muscle can be picked up for processing. Electrodes are capable of recording activity from one or a small number of nerve fibers or cell bodies. See, for example, the methods and devices described in U.S. Pat. No. 6,647,296, incorporated herein by reference in its entirety. Electrodes on the scalp or brain surface record from a large number of neurons in aggregation, providing information about the aggregate activity of large populations of neurons, as described in exemplary U.S. Pat. Nos. 5,052,401, 6,647,296, and U.S. Pat. No. 6,690,959, which are incorporated herein by reference in their entirety. Also a strain gauge attached to the muscle could be used in principle. The difficulty of these approaches is how to transfer the electric signal from the sensor in the ciliary muscle, to the processing and drive circuitry in the intra-optic lens. The invention comprising the interacting elements a) an electro-magnetic marker tag attached to the ciliary muscle, b) an electronic oscillator with (FM) demodulation circuitry on the lens and c) a coil positioned on the lens, whereby a steering signal proportional to the state of the ciliary muscle is electronically and remotely derived from the inductance of the coil generated by the changes of inductance of the sensing coil on the intra-optic lens due to position changes of the magnetic, metallic or coil tag an the ciliary muscle interaction and recovering of the information content of the inductance by the electronic demodulation circuitry to have a signal that is proportional to the position of the muscle marker tag. In present invention the state of the ciliary muscle generates a proportional steering signal based on (expressing how the brain wants the eye to accommodate) which is electronically and remotely derived, via electronic FM demodulation circuitry on the lens, from the inductance of a coil, also positioned on the lens. Our invention in an embodiment provides a non-contact mechanism, in which the changes of the state, i.e. the radial contraction distance, of the ciliary muscle, containing a ferromagnetic tracer particle attached to it, are monitored by the induced electric inductance changes in a pick-up coil placed on the intra-optic lens, in a particular design, radial motions of the tracer particle are translated into proportional inductance changes of the coil, which can be detected as amplitude modulations (AM detection) or frequency modulations (FM detection) of the oscillator built around the coil.

Example 3

Energy Source (Q)

In a particular embodiment, the electric energy, necessary to drive the electronic detection and driving circuitry, is supplied by a rechargeable battery, which can be charged via a transformer circuit between a receiving coil in the intra-optic lens and a transmitting coil in front of the eye (e.g. in the glasses or pillow of the person). Alternatively, the energy transmission can be achieved by daylight, and if necessary by sending additional, invisible infrared (IR) light from the person's glasses into the eye, to be picked up and converted to electric current in a solar cell placed on the intra-optic device. The electromagnetic interaction between a circuit in front of the person and the intra-optic device can also be used to monitor or the actions of the device, where information is transferred via AM of FM modulation of the electromagnetic waves. External control of the dioptric power of the intra-optic lens offers the possibility to measure the distance of objects of interest in the external circuit, and to send this information to the intra-optic device, in order to achieve the proper focusing. For nearby objects (<1 m), iterative fine tuning of the dioptric power in a feedback loop system is necessary for optimum image sharpness.

Although exemplary embodiments of the present invention are described above, needless to say, the invention is not restricted to the exemplary embodiments described herein; the invention can be implemented in a variety of variations. modifications, additions, or the like without departing from the scope thereof as defined by the appended claims.

REFERENCES TO THE APPLICATION

[1] T. Hellmuth et al. Sensors Update 3(1), 289-223(2001)
[2] T. Missotten, T. et al. Journal of Cataract and Refractive Surgery 30(10), 2084-2087 (2004)
[3] G. Li, D. I., Mathine, et al. Proceedings of the National Academy of Sciences of the United States of America, PNAS published online Apr. 5, 2006; doi:10.1073/pnas.0600850103
[4] United States Patent 20070129799.
[5] Naomi Sharon, et al. Experimental Eye Research 87(1), 49-55(2008)

We claim:

1. An electro-optical implant assembly, the implant assembly comprising 1) an electronic detector system or device which has a motion detector element and 2) an electro- optic artificial lens assembly and further comprising 3) a marker element having a marker or markers adapted to induce electric impedance or voltage variation on the motion detector element in relation to the positional modification or in relation to the spatiotemporal features of said marker element versus detector system to convert the electric impedance or voltage variation into a change of dioptric strength of the electro-optic artificial lens assembly, wherein the motion detector element is electronically connected with the marker element to generate a steering signal for refractive power control of the lens assembly which is representative for an optic nerve signal from the visual cortex generated from neuronal processed spatiotemporal features and to change the dioptric strength in order to get a sharp image, the marker element is electromagnetically detectable and is adapted to be monitored by induced electric inductance changes, and the marker element is one of the following elements: a paramagnetic element or a ferromagnetic element or an electrically conductive element.

2. The electro-optical implant assembly of claim 1, wherein the motion detector element comprises at least one inductive detector element.

3. The electro-optical implant assembly of claim 2, wherein the inductive detector element is or comprises any one of the following elements: an inductive coil or a wired inductive material or a deposited metal structure or a printed circuit board.

4. The electro-optical implant assembly of claim 2, wherein the inductive detector element is or comprises an inductive coil which is electronically monitored by an electronic circuit.

5. The electro-optical implant assembly of claim 4, wherein the electronic circuit is an oscillation amplitude detection circuit or an oscillation frequency detection circuit.

6. The electro-optical implant assembly according to claim 1, wherein the implant comprises a signal conversion mechanism adapted to convert the electric impedance variation into a change of dioptric strength of the electro-optic artificial lens assembly.

7. The electro-optical implant assembly according to claim 1, wherein the electro-optic artificial lens assembly comprises a refractive liquid- crystal display assembly with changeable refractive index and thus dioptric power if voltage is applied on the electrodes.

8. The electro-optical implant assembly according to claim 1, wherein the detector system is electrically or electronically connected with the electro-optic artificial lens assembly so that an electronic signal or a time-varying voltage or current that conveys information of said spatiotemporal variation of marker versus detector system is translated to a change of dioptric strength of said electro-optic artificial lens assembly.

9. The electro-optical implant assembly according to claim 1, wherein movement of the marker element modifies an electromagnetic field or oscillations in the electromagnetic field.

10. The electro-optical implant assembly according to claim 1, comprising an electro-optic self-adaptive artificial lens.

11. The electro-optical implant assembly according to claim 1, wherein said motion detector and the intra-optic lens act as a closed feedback loop allowing the person to focus on images at distances between 25 cm and infinity.

12. The electro-optical implant assembly according to claim 1, wherein the motion detector is electronically connected with the marker element to generate a time-varying voltage or current in the lens assembly to control the refractive power of the lens wherein the time-varying voltage or current conveys information of the visual cortex or its optical nerve.

13. The electro-optical implant assembly according to claim 1, wherein the detection of the electronic detection system or detection device is based on the monotonic relation between the marker position, and the electric impedance of an inductive element comprised in a detector system.

14. The electro-optical implant assembly according to claim 1 for use in a surgical treatment of a patient to restore or improve vision sharpness wherein the marker or markers are surgically placed in said patient so that the marker or markers are comprised in or are on the ciliary muscle, or near to the ciliary muscle, in the zonular fiber connection zone between the ciliary muscle and the lens body.

15. The electro-optical implant assembly according to claim 1 for use in a surgical treatment of a patient to restore or improve vision sharpness wherein after surgery the electronic detection system, in total or in part or its core, is located in the peripheral zone of the artificial intraoptic lens, out of the transparent zone which transmits the light from the outside world to the retina and wherein the marker or markers are subcutaneously or attached to the skin placed in the region between both eyes so that at turning-in of the eye balls towards the central axis in the vision direction the degree of turning-is translated in the degree of impedance variation on the motion detector element.

16. The electro-optical implant assembly according to claim 1 for use in a surgical treatment of a patient to restore or improve vision wherein after surgery the marker or markers and/or detection systems are placed between both eyes or close to the eye(s) so that turning-in of the eyes then also is reflected in the relative positions between markers and detection systems and that the derived impedance signals in the electro-optic circuitry controls the dioptric strength of the lens.

17. The electro-optical implant assembly according to claim 1 comprising a lens assembly wherein the lens assembly is a dual lens assembly with intra-optic lenses electronically controllable liquid crystal sandwiched between and aligned with transparent, electrode coated curved surfaces forming a concave lens shape where the refractive power of intra-optic lens is made polarisation independent by optically processing two orthogonal polarization components of the light in series, thus proportionally refracting all polarization components of the incident light.

18. The electro-optical implant assembly of claim 1, wherein the motion detector element is electronically connected with the marker element in a wireless manner.

19. The electro-optical implant assembly of claim 1, wherein the motion detector element comprises at least one inductive detector element being an inductive coil and an electronic circuit for electronically monitoring the inductive coil for sensing motion of the marker.

20. The electro-optical implant assembly of claim 19, wherein the motion detector element is a Colpitts oscillator.

\* \* \* \* \*